United States Patent
Borate et al.

(10) Patent No.: US 9,540,350 B2
(45) Date of Patent: Jan. 10, 2017

(54) 1-SUBSTITUTED, 4-(SUBSTITUTED PHENOXYMETHYL)-1,2,3-TRIAZOLE COMPOUNDS WITH ANTIFUNGAL PROPERTIES AND METHODS FOR PREPARATION THEREOF

(71) Applicants: FDC LIMITED, Mumbai (IN); COUNCIL OF SCIENTIFIC & INDUSTRIAL RESEARCH, New Delhi (IN)

(72) Inventors: Hanumant Bapurao Borate, Pune (IN); Ananda Shahaji Kudale, Pune (IN); Subhash Prataprao Chavan, Pune (IN); Sunita Sharad Kunte, Pune (IN); Mohan Anand Chandavarkar, Mumbai (IN); Ramkrishnan Ramachandran Iyer, Mumbai (IN); Amit Chandrakant Tawte, Mumbai (IN); Deepali Damodar Rao, Mumbai (IN)

(73) Assignees: FDC Limited, Mumbai (IN); Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/771,991

(22) PCT Filed: Feb. 21, 2014

(86) PCT No.: PCT/IN2014/000112
§ 371 (c)(1),
(2) Date: Sep. 1, 2015

(87) PCT Pub. No.: WO2014/132267
PCT Pub. Date: Sep. 4, 2014

(65) Prior Publication Data
US 2016/0009692 A1    Jan. 14, 2016

(30) Foreign Application Priority Data
Mar. 1, 2013  (IN) .......................... 626/MUM/2013

(51) Int. Cl.
| | | |
|---|---|---|
| *C07D 207/34* | (2006.01) | |
| *C07D 403/06* | (2006.01) | |
| *C07D 403/10* | (2006.01) | |
| *A01N 43/653* | (2006.01) | |
| *A61K 31/4196* | (2006.01) | |
| *A61K 31/496* | (2006.01) | |
| *C07D 403/14* | (2006.01) | |
| *C07D 409/14* | (2006.01) | |

(52) U.S. Cl.
CPC .......... *C07D 403/06* (2013.01); *A01N 43/653* (2013.01); *A61K 31/4196* (2013.01); *A61K 31/496* (2013.01); *C07D 403/10* (2013.01); *C07D 403/14* (2013.01); *C07D 409/14* (2013.01)

(58) Field of Classification Search
CPC .................................................. C07D 403/10
See application file for complete search history.

(56) References Cited

FOREIGN PATENT DOCUMENTS

| | | |
|---|---|---|
| EP | 0548553 A1 | 6/1993 |
| WO | 2008078720 A1 | 7/2008 |
| WO | 2012/047762 A2 | 4/2012 |
| WO | 2012/123952 A1 | 9/2012 |

OTHER PUBLICATIONS

International Search Report for PCT/IN2014/000112 dated Aug. 13, 2012.
Aher, et al., "Synthesis and antifungal activity of 1,2,3-triazole containing fluconazole analogues", Bioorganic & Medicinal Chemistry Letters 19(2009) 759-763.
Borate, "Fluconazole analogues containing 2H-1, 4-benzothiazin-3(4H)-one or 2H-1,4-benzoxazin-3(4H)-one moieties, a novel class of anti-Candida agents", Bioorganic & Medicinal Chemistry Letters 20 (2010) 722-725.
Borate, "Novel hybrids of fluconazole and furanones: Design, synthesis and antifungal activity", Bioorganic & Medicinal Chemistry Letters 21 (2011) 4873-4878.

(Continued)

*Primary Examiner* — Michael Barker
*Assistant Examiner* — Karen Cheng
(74) *Attorney, Agent, or Firm* — KramerAmado P.C.

(57) ABSTRACT

Disclosed herein are novel antifungal compounds of Formula 1, containing 1-substituted, 4-(substituted phenoxymethyl)-1,2,3-triazole moieties coupled to a core having triazole ring, (un)substituted phenyl ring and tertiary alcoholic functionality, and pharmaceutically acceptable salts thereof; methods for preparing these compounds; and pharmaceutical preparations containing these novel compounds for prevention and treatment of fungal infections.

Formula 1

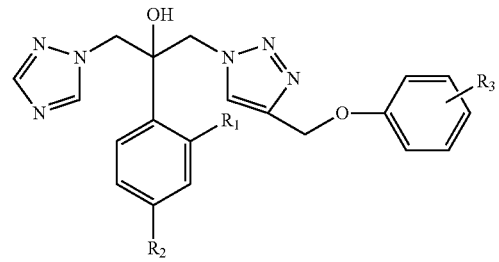

16 Claims, No Drawings

(56) References Cited

OTHER PUBLICATIONS

Katritsky, "QSAR Modeling of the antifungal activity against Candida albicans for a diverse set of organic compounds", Bioorganic & Medicinal Chemistry 16 (2008) 7055-7069.
Lebouvier, et al., "Synthesis and antifungal activities of new fluconazole analogues with azaheterocycle moiety", Bioorganic & Medicinal Chemistry Letters 17 (2007) 3686-3689.
Liu, et al., "Synthesis and SAR studies of biaryloxy-substituted triazoles as antifungal agents", Bioorganic & Medicinal Chemistry Letters, Pergamon, Elsevier Science GB, vol. 18, No. 11, Jun. 1, 2008, 3261-3265.
Patel, et al., "Design, synthesis and determination of antifungal activity of 5(6)-substituted benzotriazoles", Eur J Med Chem. Jun. 2010;45(6):2214-22.
Pore, et al., "Synthesis and antifungal activity of 1,5-disubstituted-1,2,3-triazole containing fluconazole analogues", Med.Chem.Commun., 2012, 3, 484.
Uchida, et al., "Amide analogs of antifungal dioxane-triazole derivatives: Syntehsis and in vitro activities", Bioorganic & Medicinal Chemistry Letters vol. 19, Issue 7, Apr. 1, 2009, pp. 2013-2017.
Uchida, et al., "Carbon analogs of antifungal dioxane-triazole derivatives: Synthesis and in vitro activities", Bioorganic & Medicinal Chemistry Letters vol. 18, Issue 24, Dec. 15, 2008, pp. 6538-6541.

1-SUBSTITUTED, 4-(SUBSTITUTED PHENOXYMETHYL)-1,2,3-TRIAZOLE COMPOUNDS WITH ANTIFUNGAL PROPERTIES AND METHODS FOR PREPARATION THEREOF

TECHNICAL FIELD

The present invention relates to novel antifungal compounds of Formula 1, containing 1-substituted, 4-(substituted phenoxymethyl)-1,2,3-triazole moieties and pharmaceutically acceptable salts thereof; methods for preparing these compounds; and pharmaceutical preparations containing these novel compounds for prevention and treatment of fungal infections.

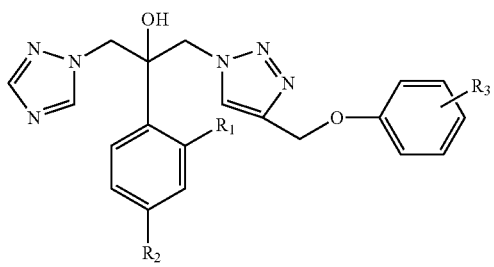

Formula 1

BACKGROUND AND PRIOR ART

Fluconazole is an important member of the azole class of antifungal agents, as it is orally active and has low toxicity, but its extensive use has resulted in emergence of fluconazole-resistant fungal strains. It is therefore necessary to develop analogues of fluconazole effective against resistant strains, and research in this direction has resulted in many new compounds containing fluconazole pharmacophores. However, to address the issues like toxicity, solubility, cost, broad spectrum of activity etc, it is necessary to develop superior antifungal agents. The structure-activity relationship studies have shown that presence of one triazole ring, halogenated phenyl ring and tertiary alcoholic oxygen functionality is necessary for antifungal activity of fluconazole or its analogues.

Some of the recent references describing synthesis and antifungal activity of fluconazole analogues are described in the following articles: Borate et al. Bioorg. Med. Chem. Lett. 21 (16), 4873-8 (2011); Borate et al. Bioorg. Med. Chem. Lett. 20, 722 (2010); Pore et al. Bioorg. Med. Chem. Lett. 19, 759 (2009); Konosu et al. Bioorg. Med. Chem. Lett. 19, 2013 (2009); Bioorg. Med. Chem. 16, 7055 (2008); Bioorg. Med. Chem. Lett. 18, 3261 (2008); Bioorg. Med. Chem. Lett. 18, 6538 (2008); Bioorg. Med. Chem. Lett. 17 (13), 3686 (2007).

WO 2012047762 discloses antifungal agents for treating infections by microorganism, wherein said antifungal agent comprises an antifungal compound containing triazole, imidazole or echinocandin moieties, linked to another antifungal or immunosuppressive compound, via a covalently-bonded linker. Thus, said PCT application teaches connecting of two active moieties via a linking moiety to obtain enhanced antifungal activity, whereas the present invention discloses coupling of one active moiety to another inactive moiety for obtaining compounds with enhanced antifungal activity.

771/DEL/2008 discloses new class of antifungal drugs for obtaining better antifungal spectrum, containing 1,2,3-triazol-1-yl or 4-yl moieties optionally substituted with bile acid or (long) alkyl chains, to obtain better antifungal spectrum, however said application does not cover antifungal compounds of present invention.

WO 2012123952 discloses enantiomers of fluconazole analogues containing thieno-[2,3-d]pyrimidin-4(3H)-one moiety as antifungal agents which are depicted as follows in formula A and formula B.

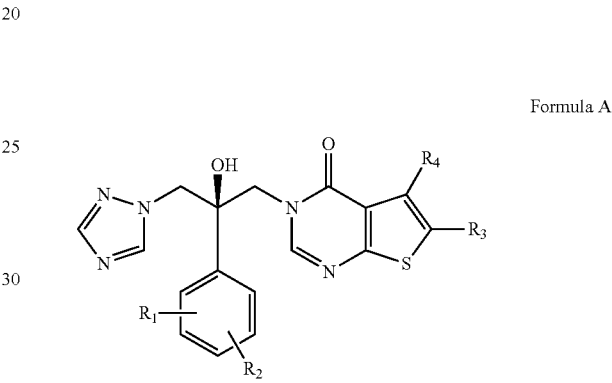

Formula A

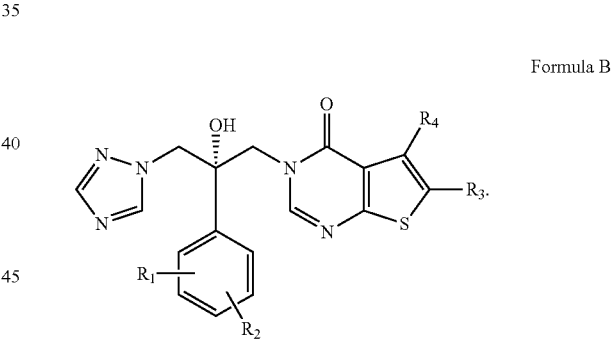

Formula B

Thus, from the aforementioned prior art, it is clear that there is still a need in the art to provide novel compounds containing fluconazole pharmacophores with superior antifungal activity, and methods for preparations thereof.

SUMMARY OF THE INVENTION

The present invention relates to novel antifungal compounds of Formula 1, containing 1-substituted, 4-(substituted phenoxymethyl)-1,2,3-triazole moieties coupled to a core having triazole ring, (un)substituted phenyl ring and tertiary alcoholic functionality, and pharmaceutically acceptable salts thereof.

Formula 1

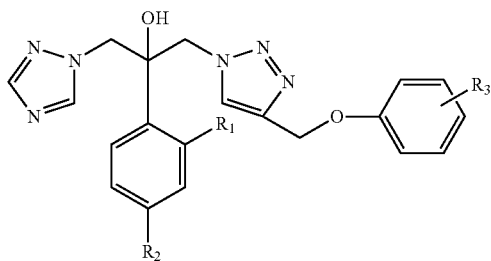

wherein,

R₁ and R₂ are same or different, and each represents hydrogen or halogen selected from fluorine, chlorine or bromine;

R₃ represents hydrogen, halogen, (un)substituted alkyl having linear or branched chain of 1 to 20 carbon atoms, (un)substituted aryl, nitro, (un)substituted alkyl/aryl/heteroaryl amino,
—C(O)R₄, —CO—CH═CHR₅, —CH═CH—COR₅ or (un)substituted alkenyl;

R₄ represents hydrogen, (un) substituted alkyl/alkenyl having linear or branched chain of 1 to 20 carbon atoms; and R₅ represents (un)substituted alkyl/aryl/heteroaryl.

The present invention further relates to methods for preparation of antifungal compounds of Formula 1, and pharmaceutical preparations containing compounds of Formula 1 for prevention and treatment of fungal infections.

DETAILED DESCRIPTION

The invention will now be described in detail in connection with certain preferred and optional embodiments, so that various aspects thereof are more fully understood and appreciated.

The present invention discloses novel antifungal compounds of Formula 1, containing 1-substituted, 4-(substituted phenoxymethyl)-1,2,3-triazole moieties coupled to a core having triazole ring, (un)substituted phenyl ring and tertiary alcoholic functionality, and pharmaceutically acceptable salts thereof; methods for preparing these compounds; and pharmaceutical preparations containing these novel compounds for prevention and treatment of fungal infections.

The compound of Formula 1 of the present invention is represented as follows;

Formula 1

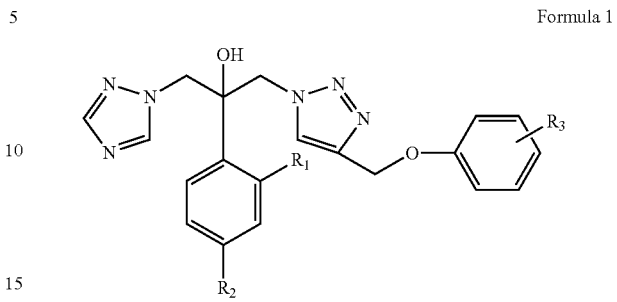

wherein,

R₁ and R₂ are same or different, and each represents hydrogen or halogen selected from fluorine, chlorine or bromine;

R₃ represents hydrogen, halogen, (un)substituted alkyl having linear or branched chain of 1 to 20 carbon atoms, (un)substituted aryl, nitro, (un)substituted alkyl/aryl/heteroaryl amino, —C(O)R₄, —CO—CH═CHR₅, —CH═CH—COR₅ or (un)substituted alkenyl;

R₄ represents hydrogen, (un) substituted alkyl/alkenyl having linear or branched chain of 1 to 20 carbon atoms; and R₅ represents (un)substituted alkyl/aryl/heteroaryl The compounds of Formula 1 are as distinguished in Table 1 as follows:

Formula 1

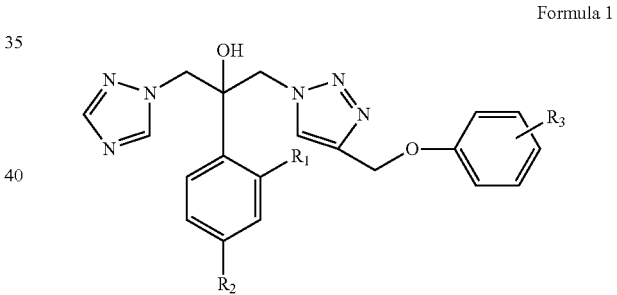

TABLE 1

| Formula 1 | R₁ and R₂ | R₃ |
|---|---|---|
| 1A | Each of R₁ and R₂ are same or different, and each represents hydrogen or halogen selected from fluorine, chlorine or bromine. | 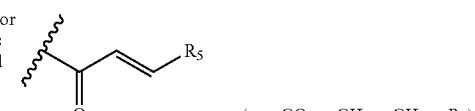 (—CO—CH═CH—R₅) [wherein R₅ represents (un)substituted alkyl/aryl/heteroaryl] |
| 1B | Each of R₁ and R₂ are same or different, and each represents hydrogen or halogen selected from fluorine, chlorine or bromine. | 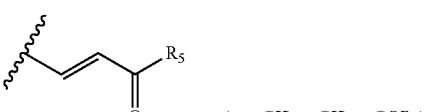 (—CH═CH—COR₅) [wherein R₅ represents (un)substituted alkyl/aryl/heteroaryl] |

TABLE 1-continued

| Formula 1 | $R_1$ and $R_2$ | $R_3$ |
|---|---|---|
| 1C | Each of $R_1$ and $R_2$ are same or different, and each represents hydrogen or halogen selected from fluorine, chlorine or bromine. | 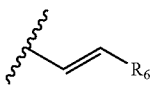 (—CH=CH—$R_6$)<br>[wherein $R_6$ represents (un)substituted alkyl/aryl/heteroaryl] |
| 1D | Each of $R_1$ and $R_2$ are same or different, and each represents hydrogen or halogen selected from fluorine, chlorine or bromine. | hydrogen,<br>halogen,<br>(un)substituted alkyl having linear or branched chain of 1 to 20 carbon atoms,<br>(un)substituted aryl,<br>nitro,<br>(un)substituted alkyl/aryl/heteroaryl amino or<br>—C(O)$R^4$ wherein $R^4$ represents hydrogen,<br>(un)substituted alkyl having linear or branched chain of 1 to 20 carbon atoms with or without double bonds |

In an embodiment, the present invention relates to the process for preparation of compounds of formula 1 as given below.

General Preparation of compounds of Formula 1:

The compounds of Formula 1 can be prepared by a method as shown in Scheme 1.

Scheme 1:

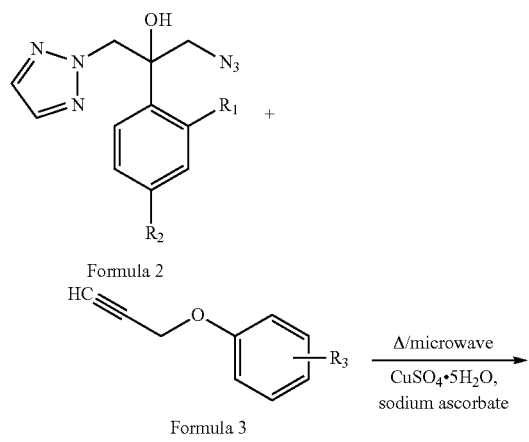

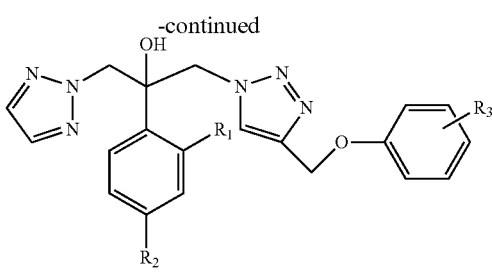

wherein $R_1$, $R_2$ and $R_3$ are as defined above.

According to Scheme 1, the compounds of Formulae 1A, 1B, 1C and 1D of the present invention are prepared by subjecting a mixture of an azide of Formula 2 with a compound of Formula 3 in a suitable solvent, in presence of copper sulphate and sodium ascorbate, under microwave conditions, or heating the stirred mixture, to obtain the compounds of Formula 1. The suitable solvent used in the reaction, is selected from dimethyl formamide, dioxane, ethanol, methanol, water, acetonitrile or mixtures thereof.

The compounds of Formulae 1A, 1B and 1C can be alternatively obtained from compounds of Formula 1D as shown in Scheme 2.

Scheme 2:

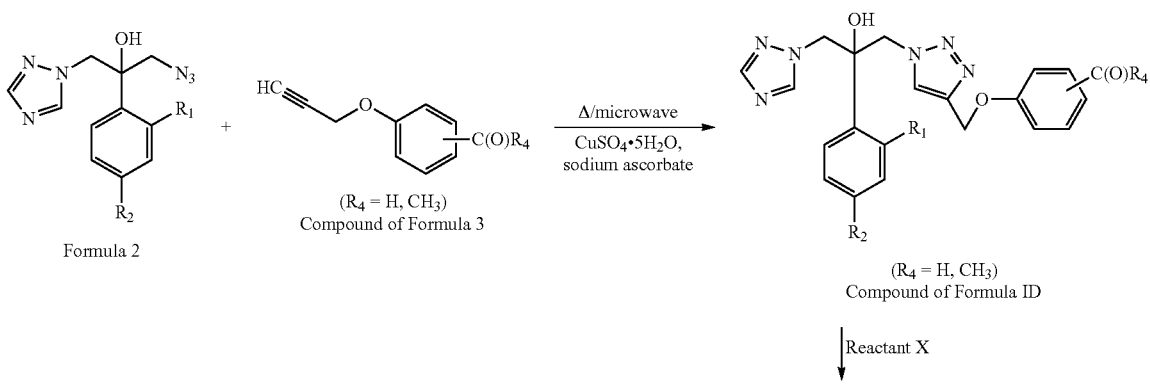

-continued

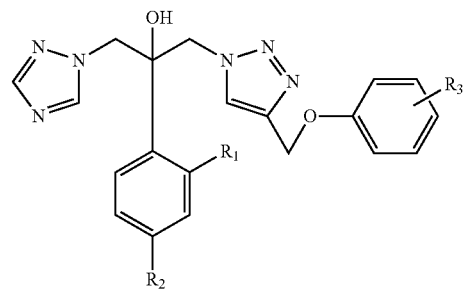

Formulae 1A, 1B & 1C wherein $R_1$, $R_2$, $R_3$ are as defined above; $R_4$ and Reactant-X are as defined in Table 2.

TABLE 2

| Formula 1 | $R_4$ | Reactant X |
|---|---|---|
| 1A | —$CH_3$ | $R_5$—CHO |
| 1B | —H | $R_5$—C(O)$CH_3$ |
| 1C | —H | $R_6$—$CH_2$CHO | wherein $R_5$ and $R_6$ are as defined in Table 1.

According to Scheme 2, the compounds of Formulae 1A, 1B, 1C of the present invention are prepared by subjecting a mixture of an azide of Formula 2 with a compound of Formula 3 in which $R_3$ is —C(O)$R_4$ wherein $R_4$ represents —H or —$CH_3$, in a suitable solvent, in presence of copper sulphate and sodium ascorbate, under microwave conditions, or heating the stirred mixture, to give a compound of Formula 1D. The resulting compound of Formula 1D is then reacted with a suitable aldehyde/ketone designated as Reactant X as specified in Table 2, in a suitable solvent, to obtain the compounds of Formulae 1A, 1B and 1C. The solvent used in above reactions is selected from dimethyl formamide, dioxane, ethanol, methanol, water, acetonitrile or mixtures thereof.

For obtaining compounds of Formula 1A from the compound of Formula 1D wherein $R_4$=$CH_3$) Reactant X used is an aldehyde as represented in Table 2, and the said reaction is carried out in the presence of a base selected from sodium hydroxide or potassium hydroxide.

For obtaining compounds of Formula 1B from the compound of Formula 1D wherein $R_4$=H, Reactant X used is a ketone as represented in Table 2, and the said reaction is carried out in the presence of a base selected from sodium hydroxide or potassium hydroxide.

For obtaining compounds of Formula 1C from the compound of Formula 1D wherein $R_4$=H, Reactant X used is an aldehyde as represented in Table 2, and the reaction is carried out in presence of malononitrile [$CH_2(CN)_2$] and a suitable base or a suitable acid or suitable amino acid(s), at a temperature of 10° to 100° C.; wherein the suitable base is selected from ammonium acetate, ammonium formate or morpholine, the suitable acid is selected from acetic acid or propanoic acid; and the amino acid(s) are selected from proline and/or alanine.

Accordingly, the various compounds of Formula 1 prepared by aforementioned processes are mentioned in Table 3.

Formula 1

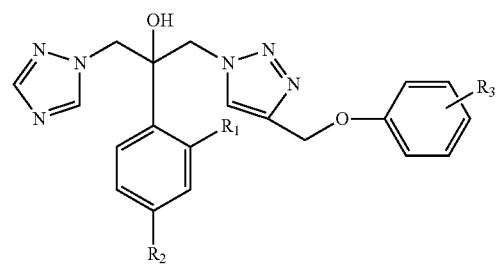

TABLE 3

| Sr. no. | Compound no. | $R_1$ | $R_2$ | $R_3$ |
|---|---|---|---|---|
| 1. | 1A-1 | F | F | 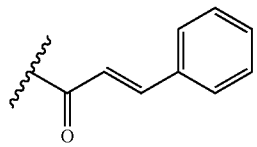 [SMILES: *C(=O)/C=C/c1ccccc1] |
| 2. | 1A-2 | F | F | 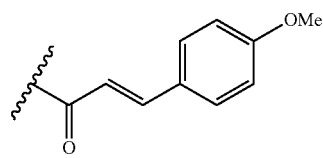 [SMILES: *C(=O)/C=C/c1ccc(OC)cc1] |

TABLE 3-continued
| Sr. no. | Compound no. | R₁ | R₂ | R₃ |
|---|---|---|---|---|
| 3. | 1A-3 | F | F | 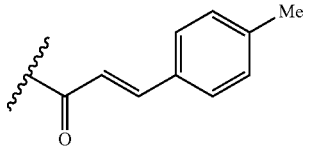 [SMILES: *C(=O)/C=C/c1ccc(C)cc1] |
| 4. | 1A-4 | F | F | 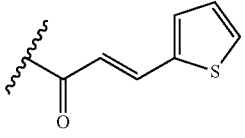 [SMILES: *C(=O)/C=C/c1cccs1] |
| 5. | 1B-1 | F | F | 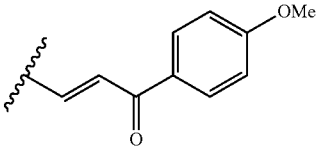 [SMILES: */C=C/C(=O)c1ccc(OC)cc1] |
| 6. | 1B-2 | F | F | 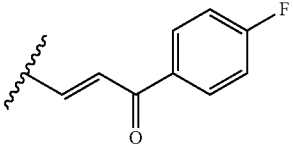 [SMILES: */C=C/C(=O)c1ccc(F)cc1] |
| 7. | 1B-3 | F | F | 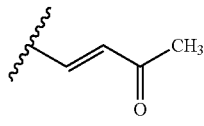 [SMILES: */C=C/C(C)=O] |
| 8. | 1B-4 | F | F | 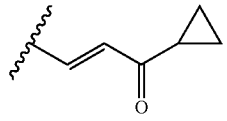 [SMILES: */C=C/C(=O)C1CC1] |
| 9. | 1B-5 | F | F | 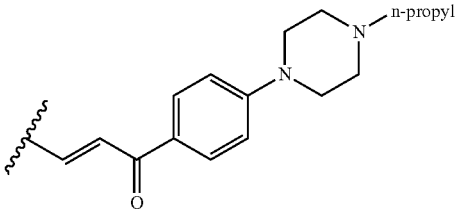 |
| 10. | 1B-6 | F | F | 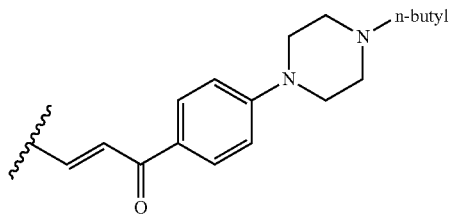 |
| 11. | 1B-7 | F | F | 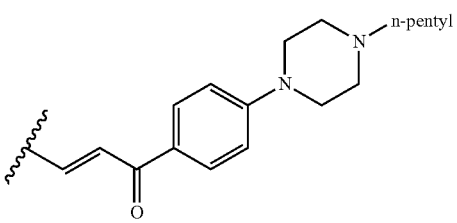 |

TABLE 3-continued
| Sr. no. | Compound no. | $R_1$ | $R_2$ | $R_3$ |
|---|---|---|---|---|
| 12. | 1B-8 | F | F | 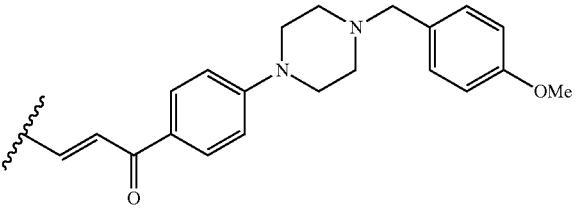 [SMILES: */C=C/C(=O)c1ccc(N2CCN(Cc3ccc(OC)cc3)CC2)cc1] |
| 13. | 1B-9 | F | F | 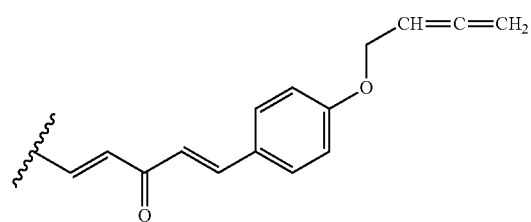 [SMILES: */C=C/C(=O)/C=C/c1ccc(OCC=C=C)cc1] |
| 14. | 1B-10 | F | F | 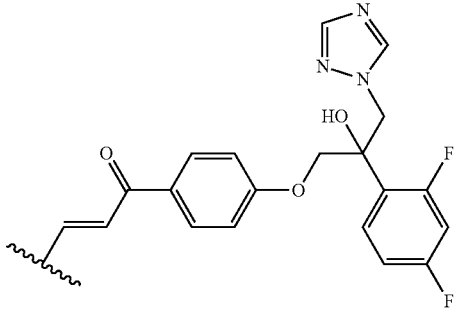 [SMILES: */C=C/C(=O)c1ccc(OCC(O)(Cn2cncn2)c2ccc(F)cc2F)cc1] |
| 15. | 1C-1 | F | F | 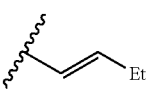 [SMILES: */C=C/CC] |
| 16. | 1C-2 | F | F | 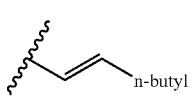 |
| 17. | 1C-3 | F | F | 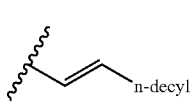 |
| 18. | 1C-4 | F | F | 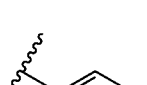 |
| 19. | 1D-1 | F | F | H |
| 20. | 1D-2 | F | F | —CH(O) |
| 21. | 1D-3 | F | F | —C(O)Me |
| 22. | 1D-4 | F | F | —NHC(O)CH$_3$ |
| 23. | 1D-5 | F | F | —CH$_3$ |
| 24. | 1D-6 | F | F | 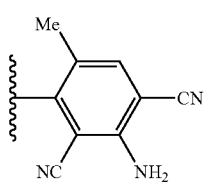 [SMILES: *c1c(C)cc(C#N)c(N)c1C#N] |

The present invention further provides pharmaceutical compositions comprising a therapeutically effective amount of a compound of Formula 1 along with one or more suitable pharmaceutical carriers/excipients.

The present invention also provides the use of compound of Formula 1 for the treatment or prevention of fungal infections.

In another aspect, the present invention provides a method of treatment or prevention of a fungal infection to a subject by administering an effective amount of the compound of Formula 1 along with one or more suitable pharmaceutical carriers/excipients. The dosage forms include solid dosage forms such as tablets, powders, capsules, liquid dosage forms as well as parenteral dosage forms. The dosage forms can also be prepared as sustained, controlled, modified and immediate release dosage forms. The active ingredient(s) and excipients can be formulated into compositions and dosage forms according to methods known in the art.

The invention is further illustrated with the following examples and should not be construed to limit the scope of the present invention. The features of the present invention will become more apparent from the following description of the inventive concept and the description of the preferred embodiments and appended claims.

EXAMPLES

Example 1

Preparation of 4-((1-(2-(2,4-difluorophenyl)-2-hydroxy-3-(1H-1,2,4-triazol-1-yl) propyl)-1H-1,2,3-triazol-4-yl)methoxy)benzaldehyde (1D-2) via heating

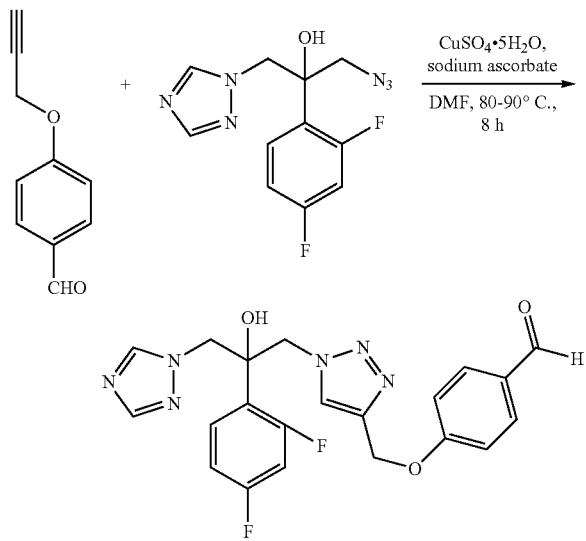

1-Azido-2-(2,4-difluorophenyl)-3-(1H-1,2,4-triazol-1-yl) propan-2-ol (0.2 g, 0.714 mmol) and 4-(prop-2-yn-1-yloxy) benzaldehyde (0.125 g, 0.785 mmol) were dissolved in 10.0 ml of dimethylformamide and copper sulphate (0.007 g, 0.0285 mmol) already dissolved in 1.0 ml of water was added to the reaction mixture followed by the addition of sodium ascorbate (0.07 g, 0.357 mmol). The reaction mixture was stirred at 80° C. for 8 h. After completion of reaction, water was added to the reaction and extracted with ethyl acetate, dried over sodium sulphate and chromatographed over silica gel using 5% methanol-ethyl acetate as an eluent to get 0.290 g (92.3%) 4-((1-(2-(2,4-difluorophenyl)-2-hydroxy-3-(1H-1,2,4-triazol-1-yl) propyl)-1H-1,2,3-triazol-4-yl)methoxy)benzaldehyde as a brownish sticky solid. $^1$H NMR (200 MHz, CDCl$_3$): δ 4.29 (d, J=16 Hz, 1H), 4.67-4.97 (m, 3H), 5.26 (s, 2H), 5.44 (s, 1H), 6.65-6.85 (m, 2H), 7.02-7.12 (m, 2H), 7.30-7.46 (m, 1H), 7.75 (s, 1H), 7.79-7.89 (m, 3H), 7.99 (s, 1H), 9.89 (s, 1H).

Example 2

Preparation of 4-((1-(2-(2,4-difluorophenyl)-2-hydroxy-3-(1H-1,2,4-triazol-1-yl) propyl)-1H-1,2,3-triazol-4-yl)methoxy)benzaldehyde (1D-2) via microwave irradiation

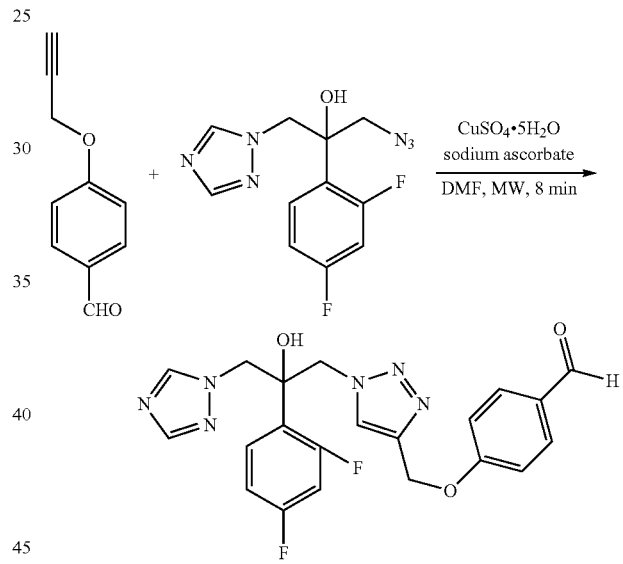

1.0 g (3.571 mmole) of 1-azido-2-(2,4-difluorophenyl)-3-(1H-1,2,4-triazol-1-yl)propan-2-ol and 0.628 g (3.928 mmole) of 4-(prop-2-yn-1-yloxy)benzaldehyde were dissolved in 8.0 ml of dimethylformamide, copper sulphate 0.035 g (0.1428 mmole) already dissolved in 2.0 ml of water was added to the reaction mixture followed by the addition of 0.353 g (1.785 mmole) of sodium ascorbate. The reaction mixture was exposed to microwave irradiation of 360 W for 8 min (1+2+2+3 min). After completion of reaction, water was added to the reaction and extracted with ethyl acetate, dried over sodium sulphate and chromatographed over silica gel using 5% methanol in ethyl acetate as an eluent to get 1.5 g (95.5%) of 4-((1-(2-(2,4-difluorophenyl)-2-hydroxy-3-(1H-1,2,4-triazol-1-yl) propyl)-1H-1,2,3-triazol-4-yl) methoxy)benzaldehyde as a brownish sticky solid. The spectral data were identical with the product obtained in Example 1.

The following compounds were prepared as per Example 1 or Example 2

2-(2,4-Difluorophenyl)-1-(4-phenyloxymethyl-1H-1,2,3-triazol-1-yl)-3-(1H-1,2,4-triazol-1-yl)propan-2-ol (1D-1)

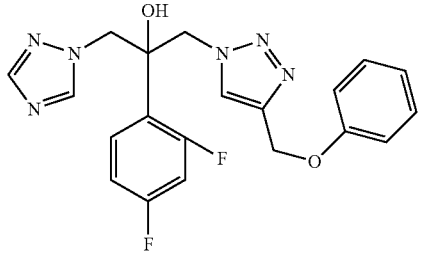 [SMILES: OC(Cn1cncn1)(Cn1cc(COc2ccccc2)nn1)c1ccc(F)cc1F]

$^1$H NMR (200 MHz, CDCl$_3$): δ 4.29 (d, J=14 Hz, 1H), 4.65-4.97 (m, 3H), 5.17 (s, 2H), 5.44 (s, 1H), 6.67-6.85 (m, 2H), 6.88-7.05 (m, 3H), 7.23-7.47 (m, 3H), 7.71 (s, 1H), 7.87 (s, 1H), 8.00 (s, 1H).

1-(4-(4-Acetylphenyloxy)methyl-1H-1,2,3-triazol-1-yl)-2-(2,4-difluorophenyl)-3-(1H-1,2,4-triazol-1-yl)propan-2-ol (1D-3)

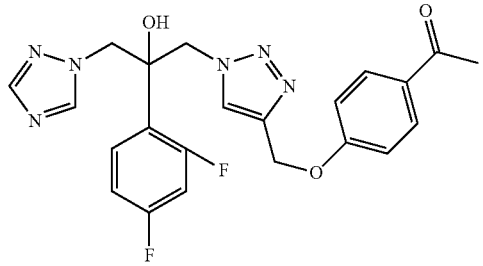 [SMILES: CC(=O)c1ccc(OCc2cn(CC(O)(Cn3cncn3)c3ccc(F)cc3F)nn2)cc1]

$^1$H NMR (200 MHz, CDCl$_3$): δ 2.56 (s, 3H), 4.29 (d, J=14 Hz, 1H), 4.67-4.97 (m, 3H), 5.23 (s, 2H), 5.44 (s, 1H), 6.65-6.85 (m, 2H), 6.94-7.05 (m, 2H), 7.30-7.46 (m, 1H), 7.74 (s, 1H), 7.83 (s, 1H), 7.88-8.04 (m, 3H).

1-(4-(4-Acetylaminophenyloxy)methyl-1H-1,2,3-triazol-1-yl)-2-(2,4-difluorophenyl)-3-(1H-1,2,4-triazol-1-yl)propan-2-ol (1D-4)

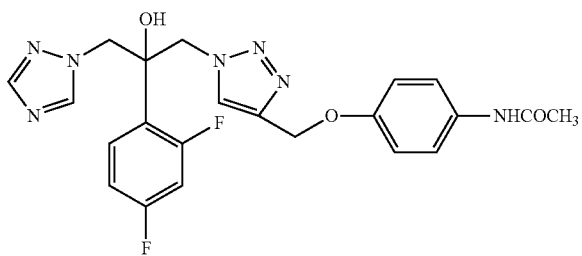

$^1$H NMR (200 MHz, CDCl$_3$): 2.14 (s, 3H), 4.30 (d, J=16 Hz, 1H), 4.65-4.95 (m, 3H), 5.12 (s, 2H), 5.49 (s, 1H), 6.65-6.93 (m, 4H), 7.29-7.50 (m, 4H), 7.69 (s, 1H), 7.82 (s, 1H), 7.99 (s, 1H).

2-(2,4-Difluorophenyl)-1-(4-(4-methylphenyloxy)methyl-1H-1,2,3-triazol-1-yl)-3-(1H-1,2,4-triazol-1-yl)propan-2-ol (1D-5)

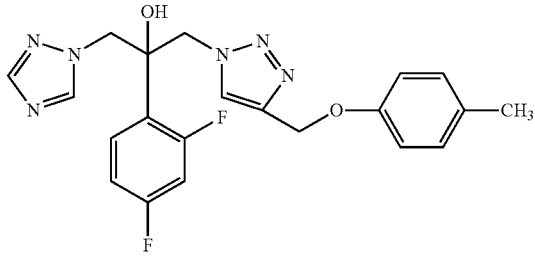 [SMILES: Cc1ccc(OCc2cn(CC(O)(Cn3cncn3)c3ccc(F)cc3F)nn2)cc1]

$^1$H NMR (200 MHz, CDCl$_3$): 2.29 (s, 3H), 4.27 (d, J=14 Hz, 1H), 4.65-4.95 (m, 3H), 5.15 (s, 2H), 5.40 (s, 1H), 6.68-6.89 (m, 4H), 7.08 (d, J=8 Hz, 2H), 7.32-7.47 (m, 1H), 7.69 (s, 1H), 7.84 (s, 1H), 7.99 (s, 1H).

Example 3

Preparation of (E)-1-(4-((1-(2-(2,4-Difluorophenyl)-2-hydroxy-3-(1H-1,2,4-triazol-1-yl)propyl)-1H-1,2,3-triazol-4-yl)methoxy)phenyl)-3-(4-methoxyphenyl)prop-2-en-1-one (1A-2)

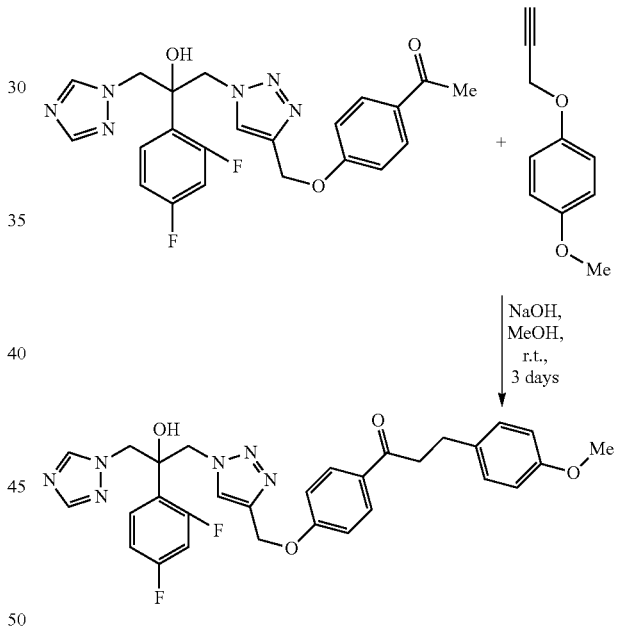

1.0 g (2.202 mmol) of 1-(4-((1-(2-(2,4-difluorophenyl)-2-hydroxy-3-(1H-1,2,4-triazol-1-yl) propyl)-1H-1,2,3-triazol-4-yl)methoxy)phenyl)-3-(4-methoxyphenyl)ethanone and 0.389 g (2.863 mmole) of anisaldehyde were dissolved in 20 ml of methanol and 0.88 g (22.02 mmole) of 10% aqueous sodium hydroxide was added drop wise and reaction was stirred at room temperature for 3 days. After completion of reaction, reaction mixture was diluted with water, methanol was removed on rotavapor, reaction mixture was cooled with ice and extracted with ethyl acetate, organic layer was dried over sodium sulphate, concentrated and chromatographed over silica gel to give 0.8 gm (63.5%) of (E)-1-(4-((1-(2-(2,4-difluorophenyl)-2-hydroxy-3-(1H-1,2,4-triazol-1-yl)propyl)-1H-1,2,3-triazol-4-yl)methoxy)phenyl)-3-(4-methoxyphenyl)prop-2-en-1-one (1A-2) as off-white sticky solid.

$^1$H NMR (200 MHz, CDCl$_3$): δ 3.86 (s, 3H), 4.29 (d, J=14 Hz, 1H), 4.67-4.97 (m, 3H), 5.25 (s, 2H), 5.45 (s, 1H), 6.66-6.85 (m, 2H), 6.88-7.09 (m, 4H), 7.30-7.49 (m, 2H), 7.60 (d, J=10 Hz, 2H), 7.79 (d, J=16 Hz, 3H), 7.95-8.08 (m, 3H).

Following compounds were prepared as per Example 3:

(E)-1-(4-((1-(2-(2,4-Difluorophenyl)-2-hydroxy-3-(1H-1,2,4-triazol-1-yl)propyl)-1H-1,2,3-triazol-4-yl)methoxy)phenyl)-3-phenylprop-2-en-1-one (1A-1)

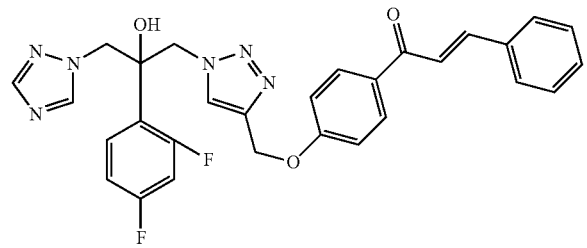 [SMILES: O=C(/C=C/c1ccccc1)c1ccc(OCc2cn(CC(O)(Cn3cncn3)c3ccc(F)cc3F)nn2)cc1]

$^1$H NMR (200 MHz, CDCl$_3$): δ 4.31 (d, J=15 Hz, 1H), 4.70-4.91 (m, 3H), 5.24 (s, 2H), 6.68-6.80 (m, 2H), 7.01-7.05 (m, 2H), 7.33-7.45 (m, 4H), 7.53 (d, J=15 Hz, 1H), 7.61-7.66 (m, 2H), 7.75 (s, 1H), 7.77-7.84 (m, 2H), 7.98-8.04 (m, 3H).

(E)-1-(4-((1-(2-(2,4-Difluorophenyl)-2-hydroxy-3-(1H-1,2,4-triazol-1-yl)propyl)-1H-1,2,3-triazol-4-yl)methoxy)phenyl)-3-(4-methylphenyl)prop-2-en-1-one (1A-3)

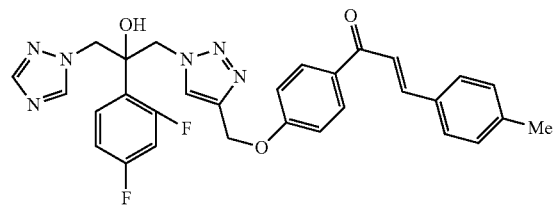 [SMILES: Cc1ccc(/C=C/C(=O)c2ccc(OCc3cn(CC(O)(Cn4cncn4)c4ccc(F)cc4F)nn3)cc2)cc1]

$^1$H NMR (200 MHz, CDCl$_3$): δ 2.40 (s, 3H), 4.28 (d, J=14 Hz, 1H), 4.66-4.97 (m, 3H), 5.26 (s, 2H), 5.43 (s, 1H), 6.66-6.85 (m, 2H), 6.98-7.09 (m, 2H), 7.18-7.48 (m, 4H), 7.50-7.59 (m, 2H), 7.76 (s, 2H), 7.84 (s, 1H), 7.95-8.08 (m, 3H).

(E)-1-(4-((1-(2-(2,4-Difluorophenyl)-2-hydroxy-3-(1H-1,2,4-triazol-1-yl)propyl)-1H-1,2,3-triazol-4-yl)methoxy)phenyl)-3-(2-thienyl)prop-2-en-1-one (1A-4)

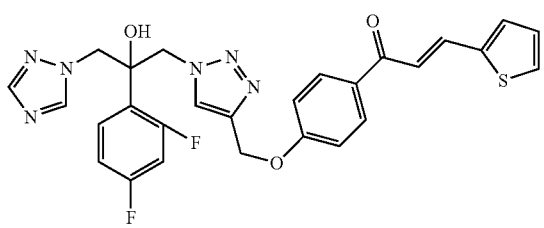 [SMILES: O=C(/C=C/c1cccs1)c1ccc(OCc2cn(CC(O)(Cn3cncn3)c3ccc(F)cc3F)nn2)cc1]

$^1$H NMR (200 MHz, CDCl$_3$): δ 4.30 (d, J=14 Hz, 1H), 4.67-4.97 (m, 3H), 5.25 (s, 2H), 5.45 (s, 1H), 6.66-6.85 (m, 2H), 6.97-7.13 (m, 3H), 7.28-7.45 (m, 4H), 7.74 (s, 1H), 7.83 (s, 1H), 7.87-8.11 (m, 4H).

Example 4

Preparation of (E)-3-(4-((1-(2-(2,4-Difluorophenyl)-2-hydroxy-3-(1H-1,2,4-triazol-1-yl) propyl)-1H-1,2,3-triazol-4-yl)methoxy)phenyl)-1-(4-(4-propylpiperazin-1-yl)phenyl)prop-2-en-1-one (1B-5) via microwave irradiation

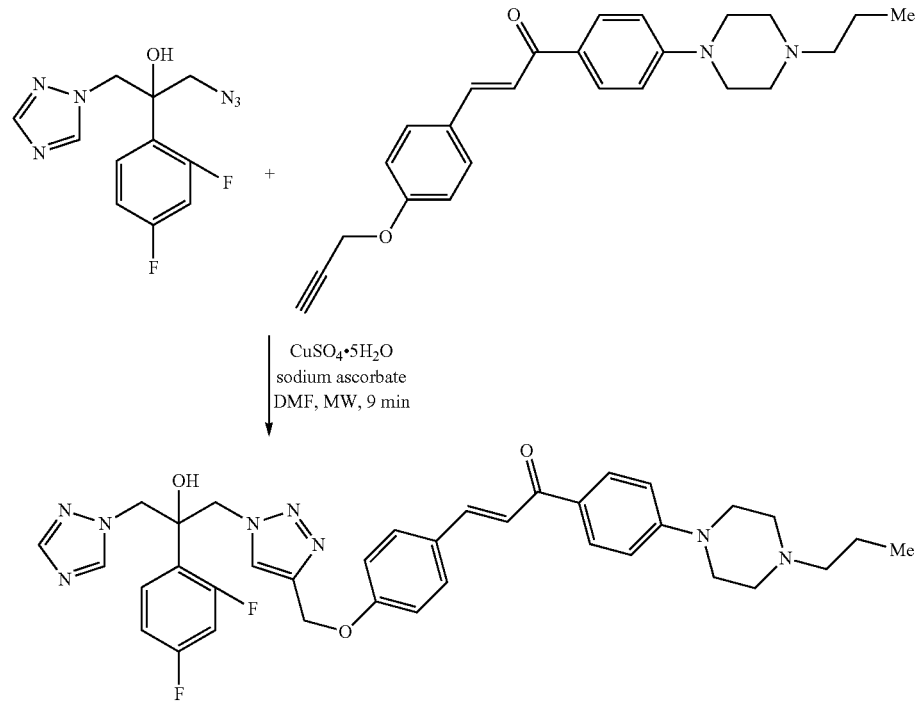

0.5 g (1.78 mmol) of 1-azido-2-(2,4-difluorophenyl)-3-(1H-1,2,4-triazol-1-yl)propan-2-ol and 0.69 g (1.78 mol) of (E)-3-(4-(prop-2-yn-1-yloxy)phenyl)-1-(4-(4-propylpiperazin-1-yl)phenyl) prop-2-en-1-one were dissolved in 8.0 ml of dimethylformamide, copper sulphate 0.017 g (0.071 mmol) already dissolved in 2.0 ml of water was added to the reaction mixture followed by the addition of 0.176 g (0.89 mmol) of sodium ascorbate. The reaction mixture was exposed to microwave irradiation of 360 W for 9 min (1, 2, 3, and 3 min). After completion of reaction, water was added to the reaction mixture and extracted with ethyl acetate, organic layer dried over sodium sulphate and chromatographed over basic alumina using 5% methanol-ethyl acetate as an eluent to get 0.6 g (69.7%) of (E)-3-(4-((1-(2-(2,4-difluorophenyl)-2-hydroxy-3-(1H-1,2,4-triazol-1-yl)propyl)-1H-1,2,3-triazol-4-yl)methoxy)phenyl)-1-(4-(4-propylpiperazin-1-yl)phenyl)prop-2-en-1-one (1B-5) as a yellow solid. $^1$H NMR (200 MHz, CDCl$_3$): δ 0.94 (t, J=8 Hz, 3H), 1.45-1.67 (m, 2H), 2.30-2.41 (m, 2H), 2.54-2.65 (m, 4H), 3.33-3.45 (m, 4H), 4.27 (d, J=14 Hz, 1H), 4.65-4.97 (m, 3H), 5.22 (s, 2H), 5.41 (s, 1H), 6.66-6.84 (m, 2H), 6.86-7.03 (m, 4H), 7.30-7.52 (m, 2H), 7.53-7.64 (m, 2H), 7.69-7.87 (m, 3H), 7.94-8.05 (m, 3H).

Example 5

Preparation of (E)-3-(4-((1-(2-(2,4-Difluorophenyl)-2-hydroxy-3-(1H-1,2,4-triazol-1-yl) propyl)-1H-1,2,3-triazol-4-yl)methoxy)phenyl)-1-(4-(4-propylpiperazin-1-yl)phenyl) prop-2-en-1-one (1B-5)

1.0 g (2.272 mmol) of 4-((1-(2-(2,4-difluorophenyl)-2-hydroxy-3-(1H-1,2,4-triazol-1-yl) propyl)-1H-1,2,3-triazol-4-yl)methoxy)benzaldehyde and 0.67 g (2.727 mmol) of 1-(4-(4-propylpiperazin-1-yl)phenyl)ethanone was dissolved in 20 ml of methanol, then 10% aqueous sodium hydroxide (0.9 g, 22.72 mmol) was added drop wise and reaction was stirred at room temperature for 3 days. After completion of reaction, methanol was removed on rotavapor and reaction mixture was cooled with ice and extracted with ethyl acetate, organic layer was dried over sodium sulphate, concentrated and chromatographed over basic alumina to get 1.0 gm (63.69%) of (E)-3-(4-((1-(2-(2,4-difluorophenyl)-2-hydroxy-3-(1H-1,2,4-triazol-1-yl)propyl)-1H-1,2,3-triazol-4-yl)methoxy)phenyl)-1-(4-(4-propylpiperazin-1-yl)phenyl) prop-2-en-1-one (1B-5) as a yellow solid. The spectral data were identical with the product obtained in Example 4.

Following compounds were prepared as per Example 5:

(E)-3-(4-((1-(2-(2,4-Difluorophenyl)-2-hydroxy-3-(1H-1,2,4-triazol-1-yl)propyl)-1H-1,2,3-triazol-4-yl)methoxy)phenyl)-1-(4-fluorophenyl)prop-2-en-1-one (1B-2)

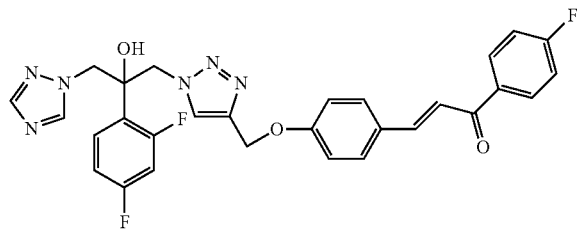 [SMILES: O=C(/C=C/c1ccc(OCc2cn(CC(O)(Cn3cncn3)c3ccc(F)cc3F)nn2)cc1)c1ccc(F)cc1]

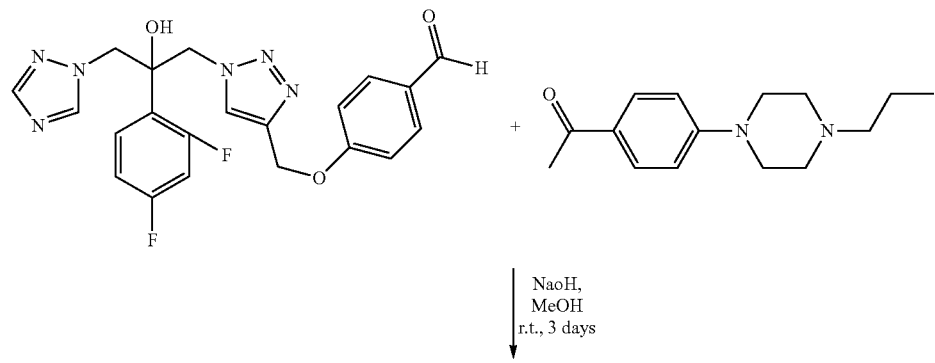

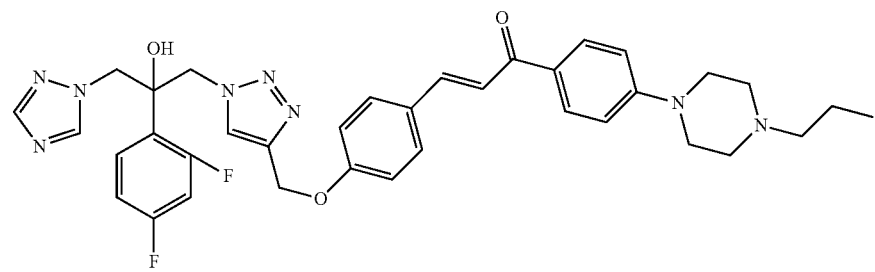

¹H NMR (200 MHz, CDCl₃): δ 4.28 (d, J=14 Hz, 1H), 4.67-4.98 (m, 3H), 5.22 (s, 2H), 5.44 (s, 1H), 6.66-6.86 (m, 2H), 6.99 (d, J=10 Hz, 2H), 7.10-7.25 (m, 2H), 7.30-7.50 (m, 2H), 7.60 (d, J=8 Hz, 2H), 7.75 (s, 2H), 7.84 (s, 1H), 7.95-8.12 (m, 3H).

(E)-1-(4-(4-n-Butylpiperazin-1-yl)phenyl)-3-(4-((1-(2-(2,4-difluorophehyl)-2-hydroxy-3-(1H-1,2,4-triazol-1-yl)propyl)-1H-1,2,3-triazol-4-yl)methoxy)phenyl)prop-2-en-1-one (1B-6)

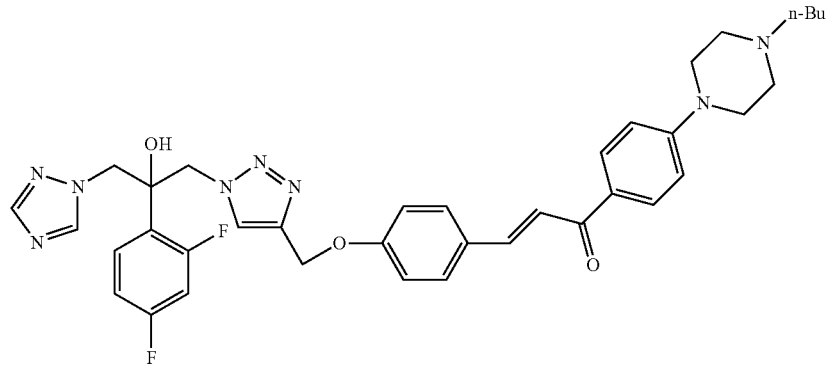

¹H NMR (200 MHz, CDCl₃): δ 0.94 (t, J=8 Hz, 3H), 1.27-1.65 (m, 4H), 2.43 (t, J=8 Hz, 2H), 2.58-2.69 (m, 4H), 3.34-3.50 (m, 4H), 4.29 (d, J=14 Hz, 1H), 4.65-4.97 (m, 3H), 5.22 (s, 2H), 5.45 (bs, 1H), 6.65-6.85 (m, 2H), 6.86-7.05 (m, 4H), 7.30-7.65 (m, 4H), 7.70-8.06 (m, 6H).

(E)-3-(4-((1-(2-(2,4-Difluorophenyl)-2-hydroxy-3-(1H-1,2,4-triazol-1-yl)propyl)-1H-1,2,3-triazol-4-yl)methoxy)phenyl)-1-(4-(4-n-pentylpiperazin-1-yl)phenyl)-prop-2-en-1-one (1B-7)

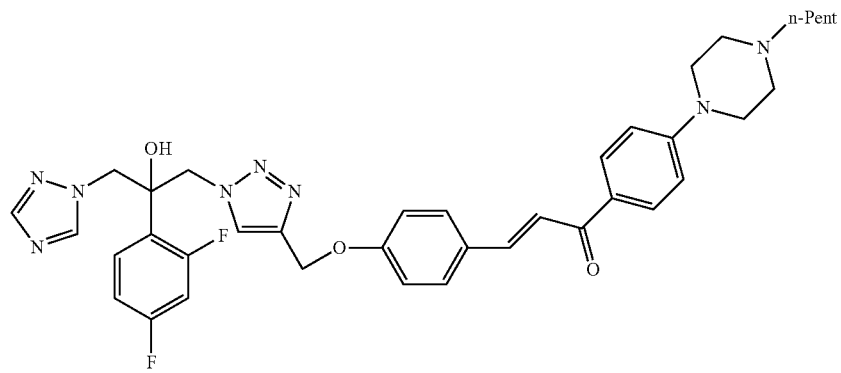

¹H NMR (200 MHz, CDCl₃): δ 0.90 (t, J=8 Hz, 3H), 1.15-1.65 (m, 6H), 2.38 (t, J=8 Hz, 2H), 2.50-2.66 (m, 4H), 3.30-3.45 (m, 4H), 4.32 (d, J=14 Hz, 1H), 4.66-4.96 (m, 3H), 5.17 (s, 2H), 5.53 (bs, 1H), 6.58-7.03 (m, 6H), 7.27-7.44 (m, 2H), 7.44-7.62 (m, 2H), 7.64-7.84 (m, 3H), 7.85-8.05 (m, 3H).

Example 6

Preparation of (E)-3-(4-((1-(2-(2,4-Difluorophenyl)-2-hydroxy-3-(1H-1,2,4-triazol-1-yl) propyl)-1H-1,2,3-triazol-4-yl)methoxy)phenyl)-1-(4-(4-(4-methoxybenzyl)piperazin-1-yl)phenyl)prop-2-en-1-one (1B-8) via heating

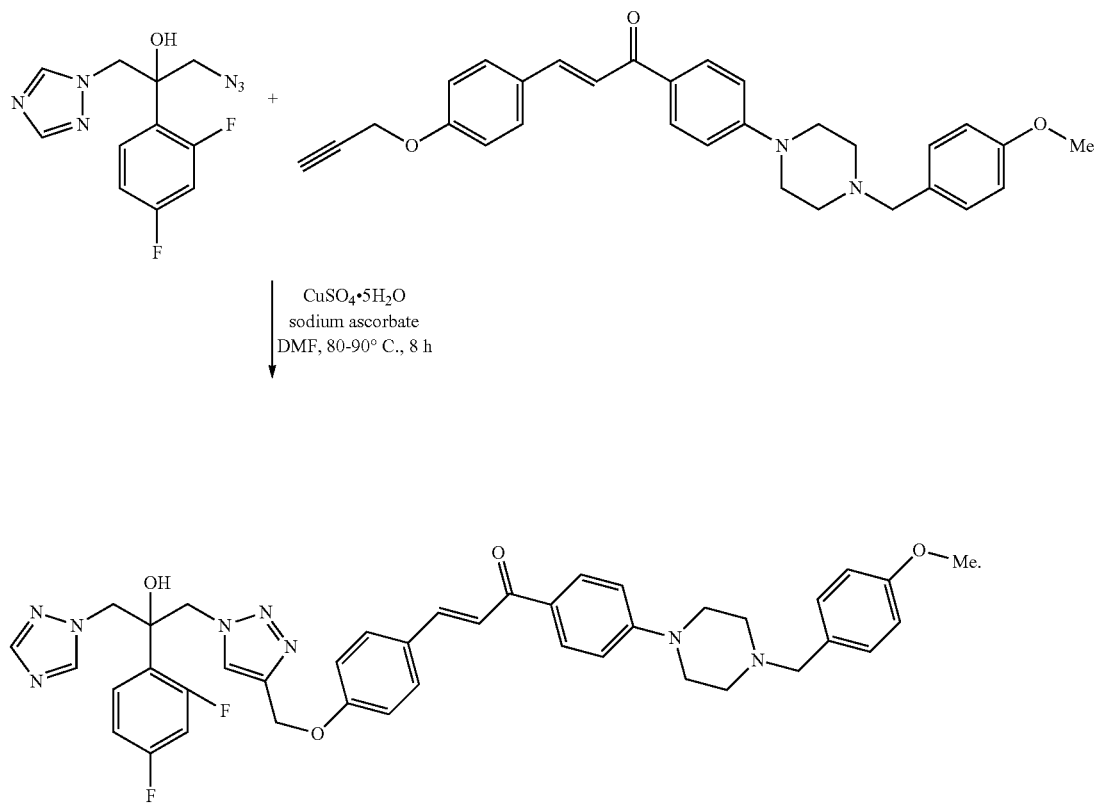

To a solution of 0.2 g (0.429 mmol) of (E)-1-(4-(4-(4-methoxybenzyl)piperazin-1-yl)phenyl)-3-(4-(prop-2-ynyloxy)phenyl)prop-2-en-1-one and 0.132 g (0.472 mmol) of 1-azido-2-(2,4-difluorophenyl)-3-(1H-1,2,4-triazol-1-yl)propan-2-ol in 10.0 ml of dimethylformamide, copper sulphate 0.004 g (0.0171 mmol) already dissolved in 1.0 ml of water was added followed by the addition of 0.042 g (0.2145 mmol) of sodium ascorbate. The reaction mixture was heated in oil bath at 80-90° C. for 8 h. After completion of reaction, water was added to the reaction mixture and extracted with ethyl acetate, dried over sodium sulphate and chromatographed over silica gel using 5% methanol in ethyl acetate as an eluent to get 0.432 g (81.2%) of (Z)-3-(4-((1-(2-(2,4-difluorophenyl)-2-hydroxy-3-(1H-1,2,4-triazol-1-yl)propyl)-1H-1,2,3-triazol-4-yl)methoxy)phenyl)-1-(4-(4-(4-methoxybenzyl)piperazin-1-yl)phenyl)prop-2-en-1-one (1B-8) as a yellow solid. $^1$H NMR (200 MHz, CDCl$_3$): δ 2.50-2.65 (m, 4H), 3.30-3.43 (m, 4H), 3.51 (s, 2H), 3.82 (s, 3H), 4.29 (d, J=14 Hz, 1H), 4.66-4.96 (m, 3H), 5.21 (s, 2H), 5.44 (s, 1H), 6.65-7.03 (m, 8H), 7.20-7.65 (m, 6H), 7.67-7.87 (m, 3H), 7.92-8.04 (m, 3H).

Example 7

Preparation of (E)-1-(4-(2-(2,4-Difluorophenyl)-2-hydroxy-3-(m-1,2,4-triazol-1-yl) propoxy)phenyl)-3-(4-((1-(2-(2,4-difluorophenyl)-2-hydroxy-3-(1H-1,2,4-triazol-1-yl) propyl)-1H-1,2,3-triazol-4-yl) methoxy)phenyl)prop-2-en-1-one (1B-10) via microwave irradiation

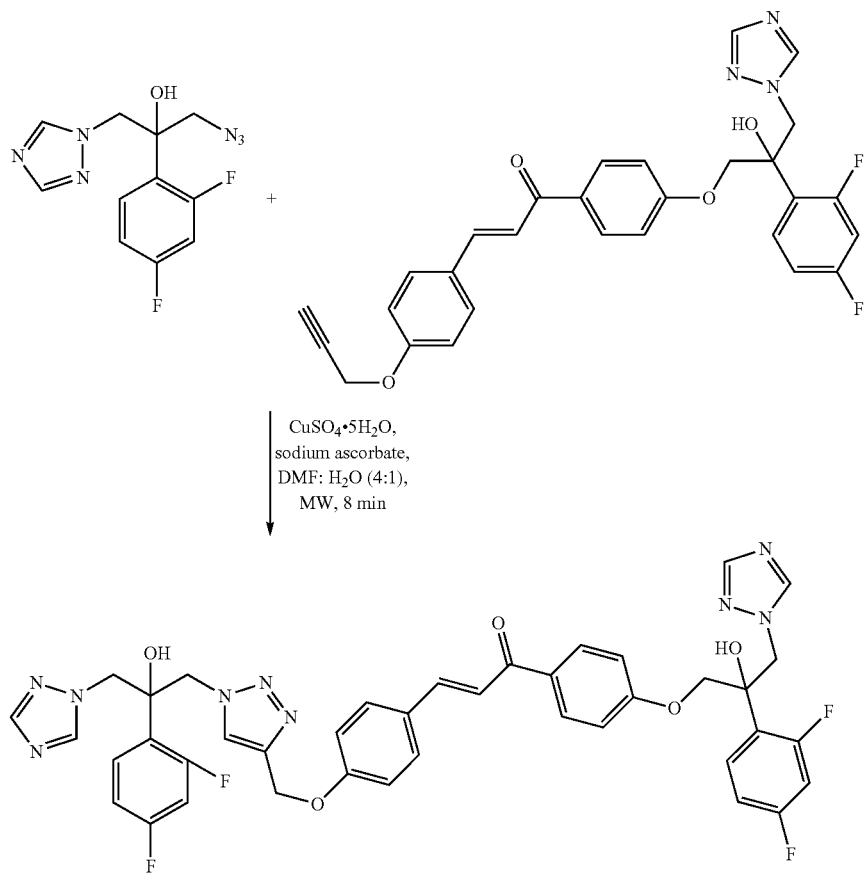

0.598 g (2.135 mmol) of 1-azido-2-(2,4-difluorophenyl)-3-(1H-1,2,4-triazol-1-yl) propan-2-ol and 1.0 g (1.941 mmol) of (E)-1-(4-(2-(2,4-difluorophenyl)-2-hydroxy-3-(1H-1,2,4-triazol-1-yl) propoxy)phenyl)-3-(4-(prop-2-yn-1-yloxy)phenyl)prop-2-en-1-one were dissolved in 8.0 ml of dimethylformamide, copper sulphate 0.019 g (0.077 mmole) already dissolved in 2.0 ml of water was added to the reaction mixture followed by the addition of 0.192 g (0.97 mmol) of sodium ascorbate. The reaction mixture was exposed to microwave irradiation of 360 W for 8 min (1, 2, 3, and 2 min). After completion of reaction, water was added to the reaction and extracted with ethyl acetate, dried over sodium sulphate and chromatographed over silica gel using 5% methanol in ethyl acetate as an eluent to get 1.2 g (77.9%) of (E)-1-(4-(2-(2,4-difluorophenyl)-2-hydroxy-3-(1H-1,2,4-triazol-1-yl) propoxy)phenyl)-3-(4-((1-(2-(2,4-difluorophenyl)-2-hydroxy-3-(1H-1,2,4-triazol-1-yl) propyl)-1H-1,2,3-triazol-4-yl)methoxy)phenyl)prop-2-en-1-one (1B-10) as a pale yellow solid. $^1$H NMR (200 MHz, CDCl$_3$): δ 4.24-4.37 (m, 3H), 4.67-4.99 (m, 6H), 5.20 (s, 2H), 5.50 (s, 1H), 6.64-7.02 (m, 8H), 7.30-7.45 (m, 2H), 7.50-7.73 (m, 5H), 7.77-7.90 (m, 2H), 7.92-8.10 (m, 4H).

Example 8

Preparation of (E)-4-(4-((1-(2-(2,4-Difluorophenyl)-2-hydroxy-3-(1H-1,2,4-triazol-1-yl) propyl)-1H-1,2,3-triazol-4-yl)methoxy)phenyl)but-3-en-2-one (1B-3)

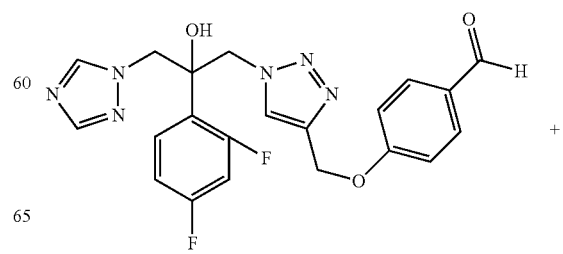

+

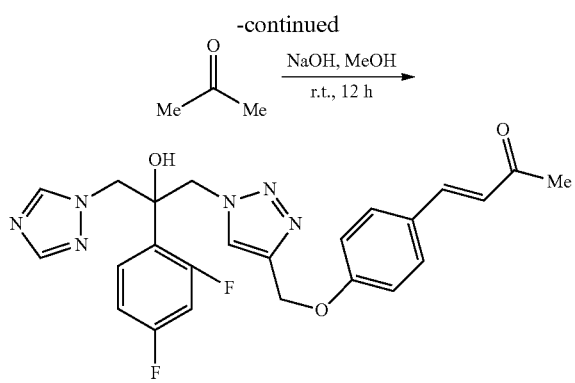

To a solution of 1.0 g (2.272 mmol) of 4-((1-(2-(2,4-difluorophenyl)-2-hydroxy-3-(1H-1,2,4-triazol-1-yl)propyl)-1H-1,2,3-triazol-4-yl)methoxy)benzaldehyde and 0.263 g (4.544 mmol) acetone in 20 ml of methanol was added drop wise 0.90 g (22.72 mmol) of 10% aqueous sodium hydroxide and reaction was stirred at room temperature for 12 h. After completion of reaction, methanol was removed on rotavapor and reaction mixture was cooled with ice and extracted with ethyl acetate, organic layer was dried over sodium sulphate, concentrated and chromatographed over basic alumina to get 0.9 gm (82.5%) of (E)-4-(4-((1-(2-(2,4-difluorophenyl)-2-hydroxy-3-(1H-1,2,4-triazol-1-yl)propyl)-1H-1,2,3-triazol-4-yl)methoxy)phenyl)but-3-en-2-one (1B-3) as off-white solid. $^1$H NMR (200 MHz, CDCl$_3$): δ 2.37 (s, 3H), 4.29 (d, J=14 Hz, 1H), 4.66-4.97 (m, 3H), 5.21 (s, 2H), 5.42 (bs, 1H), 6.55-6.85 (m, 3H), 6.90-7.05 (m, 2H), 7.30-7.55 (m, 4H), 7.73 (s, 1H), 7.84 (s, 1H), 8.00 (s, 1H).

The following compound was prepared as per Example 8:

(E)-1-(Cyclopropyl)-3-(4-((1-(2-(2,4-difluorophenyl)-2-hydroxy-3-(1H-1,2,4-triazol-1-yl) propyl)-1H-1,2,3-triazol-4-yl)methoxy)phenyl)prop-2-en-1-one (1B-4)

$^1$H NMR (200 MHz, CDCl$_3$): δ 0.92-1.00 (m, 2H), 1.08-1.16 (m, 2H), 2.17-2.27 (m, 1H), 4.93 (d, J=16 Hz, 1H), 4.70-4.91 (m, 3H), 5.17 (s, 2H), 5.55 (s, 1H), 6.65-6.81 (m, 3H), 6.93 (d, J=8 Hz, 2H), 7.30-7.40 (m, 1H), 7.45-7.60 (m, 3H), 7.71 (s, 1H), 7.80 (s, 1H), 8.00 (s, 1H).

Example 9

Preparation of (1E,4E)-1-(4-(Buta-2,3-dienyloxy)phenyl)-5-(4-((1-(2-(2,4-difluorophenyl)-2-hydroxy-3-(1H-1,2,4-triazol-1-yl)propyl)-1H-1,2,3-triazol-4-yl)methoxy)phenyl)penta-1,4-dien-3-one (1B-9)

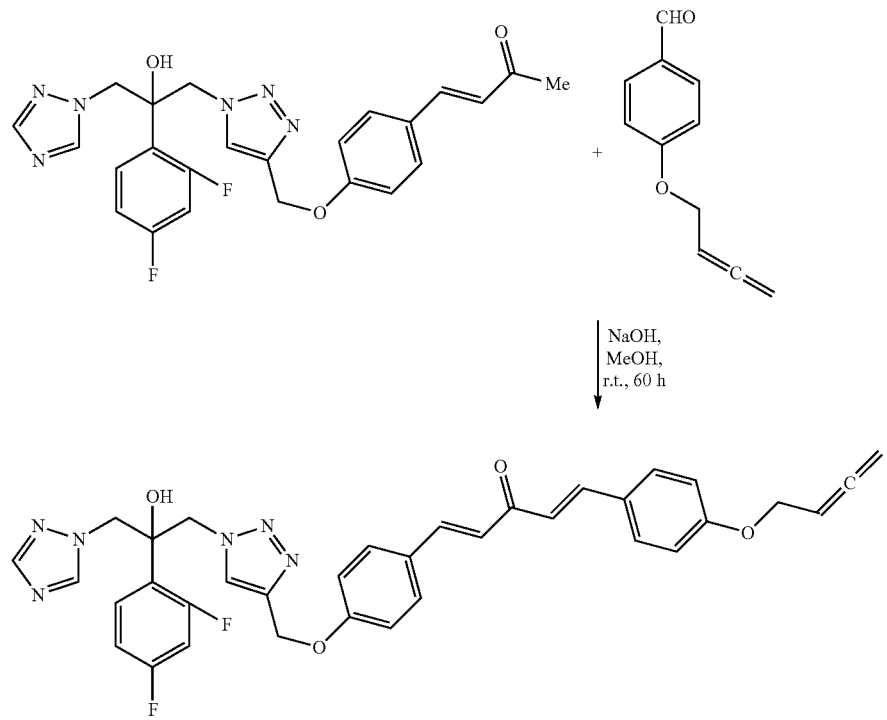 [SMILES: CC(=O)/C=C/c1ccc(OCc2cn(CC(O)(Cn3cncn3)c3ccc(F)cc3F)nn2)cc1 ; C=C=CCOc1ccc(C=O)cc1 ; C=C=CCOc1ccc(/C=C/C(=O)/C=C/c2ccc(OCc3cn(CC(O)(Cn4cncn4)c4ccc(F)cc4F)nn3)cc2)cc1]

1.0 g (2.083 mmol) of (E)-4-(4-((1-(2-(2,4-difluorophenyl)-2-hydroxy-3-(1H-1,2,4-triazol-1-yl)propyl)-1H-1,2,3-triazol-4-yl)methoxy)phenyl)but-3-en-2-one and 0.471 g (2.708 mmol) 4-(buta-2,3-dien-1-yloxy)benzaldehyde was dissolved in 20 ml of methanol, then sodium hydroxide 0.833 g (20.83 mmol) solution (10% aqueous) was added drop wise and reaction was stirred at room temperature for 60 h. After completion of reaction, methanol was removed on rotavapor, the reaction mixture was diluted with ice-cold water, extracted with ethyl acetate, organic layer was dried over sodium sulphate, concentrated and chromatographed over silica to get 0.8 gm (60.6%) of (1E,4E)-1-(4-(buta-2,3-dienyloxy)phenyl)-5-(4-((1-(2-(2,4-difluorophenyl)-2-hydroxy-3-(1H-1,2,4-triazol-1-yl)propyl)-1H-1,2,3-triazol-4-yl)methoxy)phenyl)penta-1,4-dien-3-one (1B-9) as a yellow solid. $^1$H NMR (200 MHz, CDCl$_3$): δ 4.33 (d, J=14 Hz, 1H), 4.55-4.98 (m, 5H), 5.22 (s, 2H), 5.25-5.51 (m, 2H), 5.95-6.18 (m, 1H), 6.65-6.87 (m, 3H), 6.88-7.04 (m, 6H), 7.30-7.46 (m, 1H), 7.50-7.70 (m, 4H), 7.74 (s, 2H), 7.87 (s, 1H), 8.12 (s, 1H).

Example 10

Preparation of (E)-3-(4-((1-(2-(2,4-Difluorophenyl)-2-hydroxy-3-1H-1,2,4-triazol-1-yl) propyl)-1H-1,2,3-triazol-4-yl)methoxy)phenyl)-1-(4-methoxyphenyl)prop-2-en-1-one (1B-1)

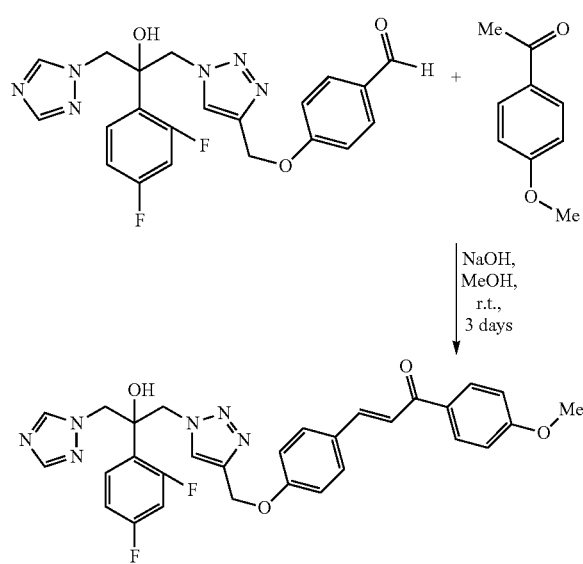

1.0 g (2.272 mmol) of 4-((1-(2-(2,4-difluorophenyl)-2-hydroxy-3-(1H-1,2,4-triazol-1-yl) propyl)-1H-1,2,3-triazol-4-yl)methoxy)benzaldehyde and 0.44 g (2.953 mmol) 1-(4-methoxyphenyl)ethanone were dissolved in 20 ml of methanol, then 0.90 g (22.72 mmol) of sodium hydroxide (10% aqueous) was added drop wise and reaction was stirred at room temperature for 3 days. After completion of reaction, methanol was removed on rotavapor and reaction mixture was cooled with ice and extracted with ethyl acetate, organic layer was dried over sodium sulphate, concentrated and chromatographed over silica to get 0.75 gm (57.6%) of (E)-3-(4-((1-(2-(2,4-difluorophenyl)-2-hydroxy-3-(1H-1,2,4-triazol-1-yl)propyl)-1H-1,2,3-triazol-4-yl)methoxy)phenyl)-1-(4-methoxyphenyl) prop-2-en-1-one (1B-1) as a off-white sticky solid. $^1$H NMR (200 MHz, CDCl$_3$): δ 3.89 (s, 3H), 4.28 (d, J=14 Hz, 1H), 4.65-4.96 (m, 3H), 5.22 (s, 2H), 5.41 (s, 1H), 6.66-6.85 (m, 2H), 6.93-7.05 (m, 4H), 7.30-7.50 (m, 2H), 7.59 (d, J=8 Hz, 2H), 7.70-7.87 (m, 3H), 7.95-8.08 (m, 3H).

Example 11

Preparation of (E)-1-(4-((4-(But-1-en-1-yl)phenoxy)methyl)-1H-1,2,3-triazol-1-yl)-2-(2,4-difluorophenyl)-3-(1H-1,2,4-triazol-1-yl)propan-2-ol (1C-1)

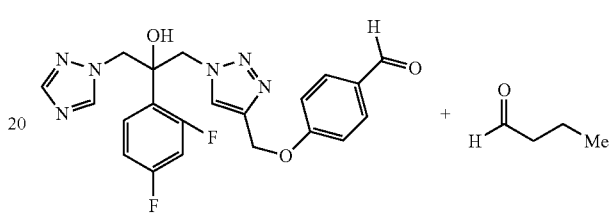

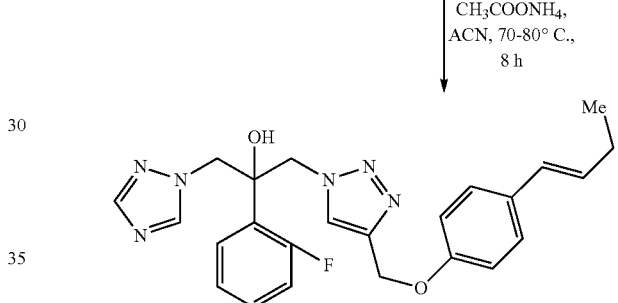

To a mixture of 4-((1-(2-(2,4-difluorophenyl)-2-hydroxy-3-(1H-1,2,4-triazol-1-yl) propyl)-1H-1,2,3-triazol-4-yl)methoxy)benzaldehyde (4.88 g, 11.1 mmol), butanal (1.0 g, 13.88 mmol) and malononitrle (1.83 g, 27.76 mmol) in 80 ml acetonitrile was added glacial acetic acid (1.249 ml, 20.82 mmol). The reaction mixture was stirred for 10 min and then ammonium acetate (1.06 g, 13.88 mmol) was added. The reaction was stirred at 75-80° C. for 8 h. The mixture was then allowed to come to room temperature, filtered through Whatman filter paper and filtrate was evaporated on rotavapor. Then water was added and the product was extracted with ethyl acetate. The organic extract was evaporated, dried over sodium sulphate and purified over silica gel (60-120 mesh) using ethyl acetate-pet ether (20% ethyl acetate in pet ether) as an eluent to give (E)-1-(4-((4-(but-1-en-1-yl)phenoxy)methyl)-1H-1,2,3-triazol-1-yl)-2-(2,4-difluorophenyl)-3-(1H-1,2,4-triazol-1-yl)propan-2-ol (1C-1) as a pale yellow thick liquid (3.2 g, 62.0%). $^1$H NMR (200 MHz, CDCl$_3$): δ 1.08 (t, J=7 Hz, 3H), 2.21 (quint, J=7 Hz, 2H), 4.26 (d, J=14 Hz, 1H), 4.64-4.97 (m, 3H), 5.17 (s, 2H), 5.39 (s, 1H), 6.13 (dt, J=16, 6 Hz, 1H), 6.32 (d, J=16 Hz, 1H), 6.67-6.80 (m, 2H), 6.86 (d, J=9 Hz, 2H), 7.26 (d, J=9 Hz, 2H), 7.30-7.45 (m, 1H), 7.70 (s, 1H), 7.84 (s, 1H), 7.98 (s, 1H).

The following compounds were prepared as per Example 11:

(E)-2-(2,4-Difluorophenyl)-1-(4-((4-(n-hex-1-en-1-yl)phenoxy)methyl)-1H-1,2,3-triazol-1-yl)-3-(1H-1,2,4-triazol-1-yl)propan-2-ol (1C-2)

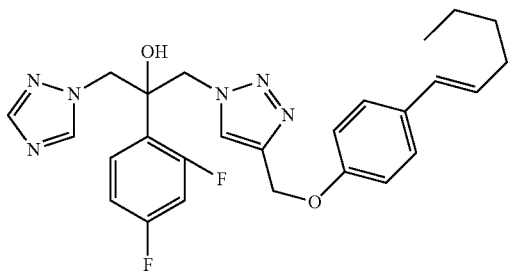 [SMILES: CCCC/C=C/c1ccc(OCc2cn(CC(O)(Cn3cncn3)c3ccc(F)cc3F)nn2)cc1]

$^1$H NMR (200 MHz, CDCl$_3$): δ 0.92 (t, J=7 Hz, 3H), 1.28-1.53 (m, 4H), 2.18 (q, J=7 Hz, 2H), 4.27 (d, J=14 Hz, 1H), 4.64-4.95 (m, 3H), 5.15 (s, 2H), 5.44 (s, 1H), 6.08 (dt, J=16, 7 Hz, 1H), 6.31 (d, J=16 Hz, 1H), 6.86 (d, J=8 Hz, 2H), 7.25 (d, J=8 Hz, 2H), 7.30-7.46 (m, 1H), 7.69 (s, 1H), 7.83 (s, 1H), 7.98 (s, 1H).

(E)-2-(2,4-Difluorophenyl)-1-(4-((4-(n-dodec-1-en-1-yl)phenoxy)methyl)-1H-1,2,3-triazol-1-yl)-3-(1H-1,2,4-triazol-1-yl)propan-2-ol (1C-3)

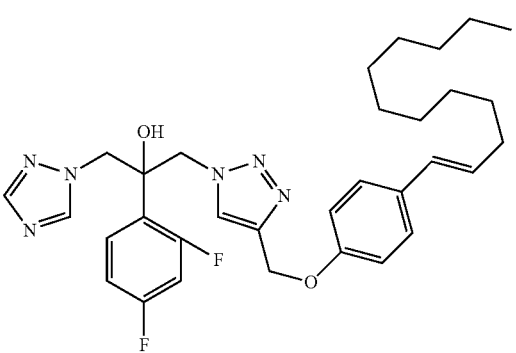 [SMILES: CCCCCCCCCC/C=C/c1ccc(OCc2cn(CC(O)(Cn3cncn3)c3ccc(F)cc3F)nn2)cc1]

$^1$H NMR (200 MHz, CDCl$_3$): δ 0.88 (t, J=7 Hz, 3H), 1.10-1.50 (m, 16H), 2.18 (q, J=7 Hz, 2H), 4.26 (d, J=14 Hz, 1H), 4.65-4.95 (m, 3H), 5.17 (s, 2H), 5.37 (s, 1H), 6.09 (dt, J=16, 7 Hz, 1H), 6.32 (d, J=16 Hz, 1H), 6.67-6.80 (m, 2H), 6.86 (d, J=8 Hz, 2H), 7.26 (d, J=8 Hz, 2H), 7.30-7.42 (m, 1H), 7.70 (s, 1H), 7.84 (s, 1H), 7.98 (s, 1H).

(E)-2-(2,4-Difluorophenyl)-1-(4-((4-(prop-1-en-1-yl)phenoxy)methyl)-1H-1,2,3-triazol-1-yl)-3-(1H-1,2,4-triazol-1-yl)propan-2-ol (1C-4)

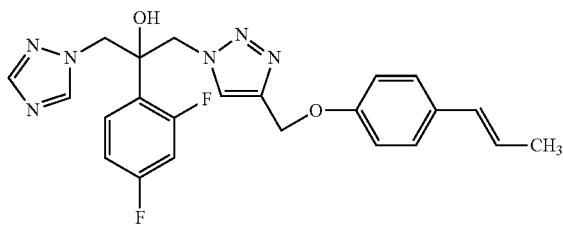 [SMILES: C/C=C/c1ccc(OCc2cn(CC(O)(Cn3cncn3)c3ccc(F)cc3F)nn2)cc1]

$^1$H NMR (200 MHz, CDCl$_3$): 1.86 (d, J=6 Hz, 3H), 4.28 (d, J=14 Hz, 1H), 4.65-4.95 (m, 3H), 5.16 (s, 2H), 5.42 (s, 1H), 6.09 (dq, J=16, 6 Hz, 1H), 6.34 (d, J=16 Hz, 1H), 6.65-6.82 (m, 2H), 6.86 (d, J=8 Hz, 2H), 7.24 (d, J=8 Hz, 2H), 7.30-7.45 (m, 1H), 7.69 (s, 1H), 7.83 (s, 1H), 7.98 (s, 1H).

Example 12

Preparation of 3-Amino-4'-((1-(2-(2,4-difluorophenyl)-2-hydroxy-3-(1H-1,2,4-triazol-1-yl)propyl)-1H-1,2,3-triazol-4-yl)methoxy)-6-methylbiphenyl-2,4-dicarbonitrile (1D-6)

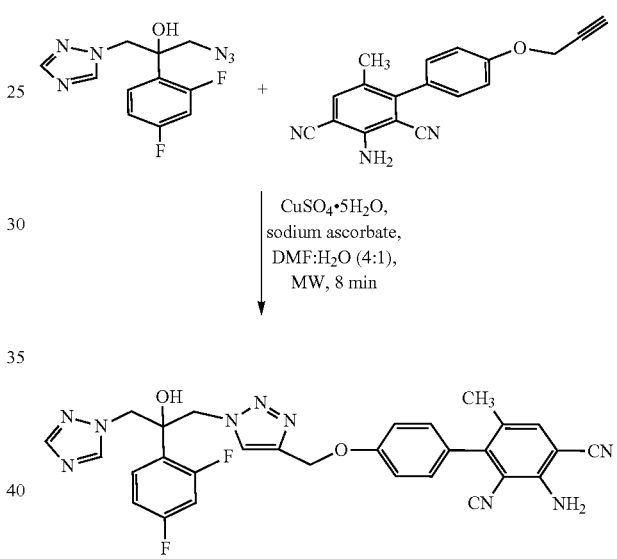

1-Azido-2-(2,4-difluorophenyl)-3-(1H-1,2,4-triazol-1-yl)propan-2-ol (200 mg, 0.71 mmol) and 3-amino-6-methyl-4'-(prop-2-ynyloxy)biphenyl-2,4-dicarbonitrile 205 mg, 0.71 mmol) were dissolved in 10.0 ml of dimethylformamide, copper sulphate (7 mg, 0.028 mmol) already dissolved in 2.0 ml of water was added to the reaction mixture followed by the addition of sodium ascorbate (70 mg, 0.35 mmol). The reaction mixture was exposed to microwave irradiation of 360 W for 8 min (1, 2, 3, and 2 min). After completion of reaction, water was added to the reaction and extracted with ethyl acetate, dried over sodium sulphate and chromatographed over silica gel using 5% methanol in ethyl acetate as an eluent to get 150 mg (27.2%) of 1D-6 as off-white solid. $^1$H NMR (200 MHz, CDCl$_3$+DMSO-d$_6$): 2.34 (s, 3H), 4.34 (d, J=16 Hz, 1H), 4.39-4.75 (m, 3H), 4.92 (s, 2H), 5.43 (bs, 2H), 5.91 (s, 1H), 6.35-6.66 (m, 2H), 6.80 (d, J=8 Hz, 2H), 6.93 (d, J=8 Hz, 2H), 6.99-7.10 (m, 1H), 7.22 (s, 1H), 7.54 (s, 1H), 7.55 (s, 1H), 7.94 (s, 1H).

Example 13

Preparation of 1-azido-2-(2,4-difluorophenyl)-3-(1H-1,2,4-triazol-1-yl)propan-2-ol [2-1]

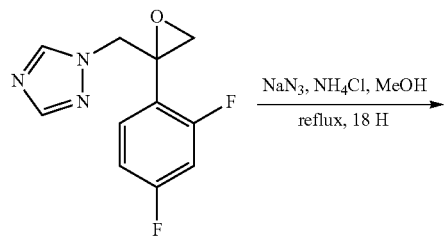

15.0 g (63.2 mmol) of 1-((2-(2,4-difluorophenyl)oxiran-2-yl)methyl)-1H-1,2,4-triazole was dissolved in 150 ml of dry methanol, 12.34 g (189.0 mmol) of sodium azide was added followed by the addition of 7.37 g (139.0 mmol) of ammonium chloride. The mixture was stirred under reflux for 18 h. After completion of reaction, the content was allowed to cool to room temperature and methanol was removed on rotavapor, 100 ml of water was added and organic compound was extracted with ethyl acetate. The organic layer was dried over sodium sulphate, concentrated and purified over silica gel using 30% ethyl acetate-pet ether as an eluent to get 15.0 gm (84.65%) 1-azido-2-(2,4-difluorophenyl)-3-(1H-1,2,4-triazol-1-yl)propan-2-ol (2-1) as a off-white crystalline solid. $^1$H NMR (200 MHz, CDCl$_3$): δ 3.53 (d, J=14 Hz, 1H), 3.69 (d, J=14 Hz, 1H), 4.69 (d, J=16 Hz, 1H), 4.78 (d, J=16 Hz, 1H), 5.09 (bs, 1H), 6.73-6.87 (m, 2H), 7.46-7.59 (m, 1H), 7.84 (s, 1H), 8.08 (s, 1H).

Example 14

Preparation of 2-(2,4-Difluorophenyl)-1-(4-(hydroxymethyl)-1H-1,2,3-triazol-1-yl)-3-(1H-1,2,4-triazol-1-yl)propan-2-ol (8A-1)

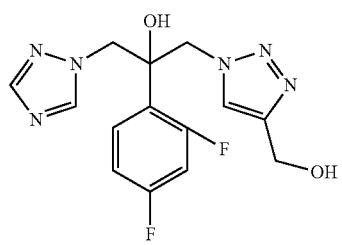 [SMILES: OCc1cn(CC(O)(Cn2cncn2)c2ccc(F)cc2F)nn1]

2.6 g (9.28 mmol) of 1-azido-2-(2,4-difluorophenyl)-3-(1H-1,2,4-triazol-1-yl)propan-2-ol and 0.623 g (11.14 mmol) of propargyl alcohol was dissolved in 50 ml of t-butanol and then 50 ml of water containing 0.788 g (3.15 mmol) of copper sulphate was added followed by the addition of 1.35 g (6.86 mmol) of sodium ascorbate. The reaction mixture was stirred at room temperature for 8 h. After completion of reaction, reaction mixture was taken in excess of ethyl acetate, water washing was given and organic layer was concentrated on rotavapor to get 2.0 g (64.1%) of 2-(2,4-difluorophenyl)-1-(4-(hydroxymethyl)-1H-1,2,3-triazol-1-yl)-3-(1H-1,2,4-triazol-1-yl)propan-2-ol (8A-1) as a off-white solid. $^1$H NMR (200 MHz, DMSO-d$_6$): δ 4.42 (d, J=6 Hz, 2H), 4.46-5.01 (m, 4H), 5.15 (t, J=6 Hz, 1H), 6.46 (s, 1H), 6.79-6.93 (m, 1H), 7.00-7.31 (m, 2H), 7.74 (s, 1H), 7.83 (bs, 1H), 8.38 (bs, 1H).

Example 15

Preparation of 1-(4-(Piperazin-1-yl)phenyl)ethanone

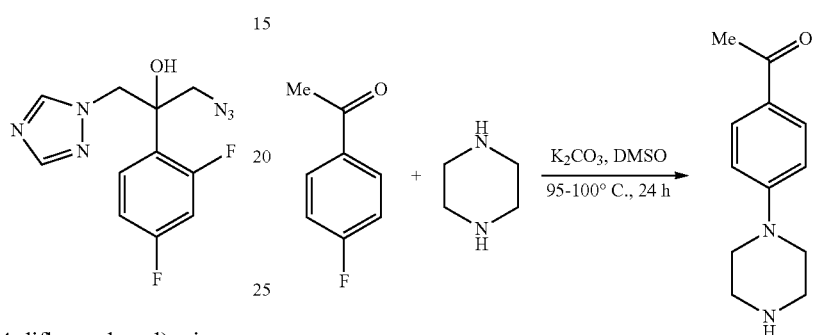

Potassium carbonate (2.99 g, 0.0217 9 mol) was taken in round bottom flask and dried with hot gun under vacuum. Tetra-butylammonium bromide (0.045 g, 0.0014 mol) was added followed by addition of piperazine (1.54 g, 0.018 mol) dissolved in dry dimethyl sulphoxide (5 ml). Reaction mixture was stirred at 80° C. and then 4-fluoroacetophenone (2 g, 0.0144 mol) was added and reflux was continued for 15 h at same temperature. It was then cooled to room temperature, diluted with water, filtered, filtrate was acidified with dil. HCl, extracted with ethyl acetate and aqueous layer was basified with dil. NaOH. It was then extracted with CHCl$_3$, CHCl$_3$ layer dried over Na$_2$S$_4$ and concentrated to get pale yellow solid (2.23 g, 75.25%, M.P. 109° C.). $^1$H NMR (200 MHz, CDCl$_3$): δ 1.91 (s, 1H), 2.52 (s, 3H), 2.98-3.05 (m, 4H), 3.28-3.35 (m, 4H), 6.87 (d, J=10 Hz, 2H), 7.87 (d, J=10 Hz, 2H).

Example 16

Preparation of 1-(4-(4-Propylpiperazin-1-yl)phenyl)ethanone

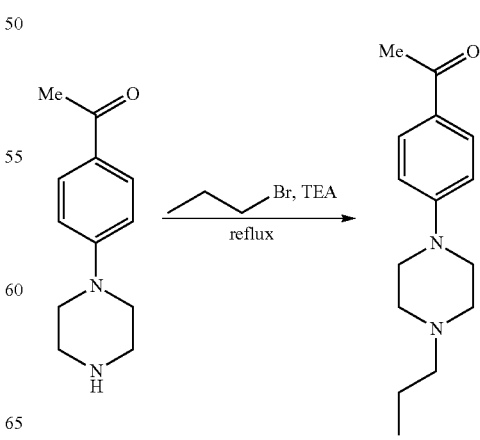

2.0 g (0.0098 mol) of 1-(4-(piperazin-1-yl)phenyl)ethanone was dissolved in 40 ml of dry acetonitrile. Then 1.77 ml (0.0196 mol) of propyl bromide was added followed by the addition of 4.24 ml (0.029 mol) of triethyl amine. The reaction mixture was refluxed for 18 h. After completion of reaction, the content was allowed to cool to room temperature and acetonitrile was removed on rotavapor. The crude product was washed with 5% ethyl acetate in pet-ether to get 2.1 gm (87.50%) 1-(4-(4-propylpiperazin-1-yl)phenyl) ethanone as a off-white solid. $^1$H NMR (200 MHz, CDCl$_3$): δ 0.93 (t, J=7 Hz, 3H), 1.45-1.65 (m, 2H), 2.30-2.42 (m, 2H), 2.51-2.62 (m, 7H), 3.37 (t, J=6 Hz, 4H), 6.87 (d, J=10 Hz, 2H), 7.87 (d, J=10 Hz, 2H).

Example 17

Preparation of (E)-3-(4-(Prop-2-yn-1-yloxy)phenyl)-1-(4-(4-propylpiperazin-1-yl)phenyl)prop-2-en-1-one (6A-1)

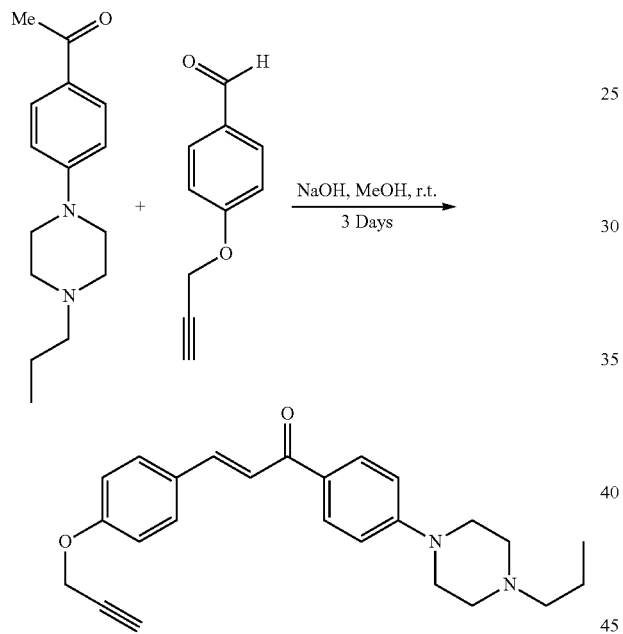

1.0 g (0.004 mol) of 1-(4-(4-propylpiperazin-1-yl)phenyl) ethanone and 1.30 g (0.0081 mol) were dissolved in 40 ml of methanol followed by the addition of 1.6 g (0.040 mol) of sodium hydroxide as a 10% solution drop-wise and reaction was stirred for three days. After completion of reaction, the precipitate of the product was filtered through Whatmann filter paper and solid was washed 3-4 times by 10% ethyl acetate in pet-ether to get 1.2 g (76.43%) of (E)-3-(4-(prop-2-yn-1-yloxy)phenyl)-1-(4-(4-propylpiperazin-1-yl)phenyl) prop-2-en-1-one (6A-1) as a yellow solid. $^1$H NMR (200 MHz, CDCl$_3$): δ 0.94 (t, J=8 Hz, 3H), 1.45-1.67 (m, 2H), 2.32-2.41 (m, 2H), 2.54-2.62 (m, 5H), 3.36-3.43 (m, 4H), 4.74 (d, J=2 Hz, 2H), 6.91 (d, J=10 Hz, 2H), 7.01 (d, J=8 Hz, 2H), 7.46 (d, J=16 Hz, 1H), 7.61 (d, J=10 Hz, 2H), 7.77 (d, J=16 Hz, 1H), 7.99 (d, J=8 Hz, 2H).

Example 18

Antifungal Activity Testing

The compounds of Formula 1 were tested for antifungal activity against *Candida albicans, C. glabrata, C. krusei, C. tropicalis, Cryptococcus neoformans, Aspergillus fumigatus, A. niger* and *Fusarium proliferatum*. In vitro evaluation of antifungal activity was performed by determining the minimum inhibitory concentration (MIC) following standard methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002). Antifungal susceptibility testing of these anti-fungal compounds was done by broth dilution method using RPMI 1640 medium with MOPS buffer. Known anti-fungal agent fluconazole was used as positive control. End points were determined after 48 hours visually and by using spectrophotometer wherever necessary. Different dilutions were tried and various sets of experiments performed. The activity parameters are enumerated in Table 4.

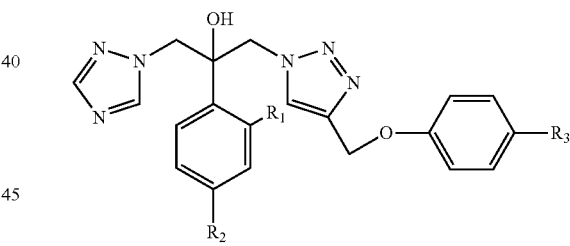

TABLE 4

| Sr. no | Compd. no. | Structure | | Activity against organisms (MIC$_{50}$ in µg/ml) | | | | | | | |
|---|---|---|---|---|---|---|---|---|---|---|---|
| | | | | Ca01 | Cg01 | Ck01 | Ct01 | Cn01 | An01 | Afm01 | Fp01 |
| | Fluconazole | | | 0.25 | 1 | 32 | 1 | 2 | >128 | >128 | >128 |
| 1. | 1D-3 | R$_1$ = R$_2$ = F; R$_3$ = —C(O)Me | | 0.5 | 1 | 64 | 4 | 4 | >128 | >128 | >128 |
| 2. | 1D-2 | R$_1$ = R$_2$ = F; R$_3$ = —CHO | | 0.5 | 1 | 64 | 2 | 4 | >128 | >128 | >128 |
| 3. | 1D-1 | R$_1$ = R$_2$ = F; R$_3$ = H | | 0.25 | 0.25 | >128 | 2 | 4 | >128 | >128 | >128 |
| 4. | 1C-1 | R$_1$ = R$_2$ = F; R$_3$ = —CH=CH—Et | | 0.03 | 0.015 | 2 | 0.25 | 0.12 | 8 | 8 | >16 |
| 5. | 1C-2 | R$_1$ = R$_2$ = F; R$_3$ = —CH=CH-n-butyl | | 0.12 | 0.06 | 2 | 1 | 0.25 | 4 | 4 | >4 |
| 6. | 1C-3 | R$_1$ = R$_2$ = F; R$_3$ = —CH=CH-n-decyl | | 1 | 0.12 | >2 | >2 | 0.5 | >2 | >2 | >2 |
| 7. | 1C-4 | R$_1$ = R$_2$ = F; R$_3$ = —CH=CHCH$_3$ | | 0.03 | 0.06 | 8 | 0.12 | 0.5 | 64 | 32 | >32 |

TABLE 4-continued
| Sr. no | Compd. no | Structure | Ca01 | Cg01 | Ck01 | Ct01 | Cn01 | An01 | Afm01 | Fp01 |
|---|---|---|---|---|---|---|---|---|---|---|
| 8. | 1D-4 | $R_1 = R_2 = F$; $R_3 = $ —NHC(O)CH$_3$ | 32 | 32 | >128 | >128 | >128 | >128 | >128 | >128 |
| 9. | 1D-5 | $R_1 = R_2 = F$; $R_3 = $ —CH$_3$ | 0.12 | 0.03 | 8 | 0.5 | 2 | 64 | 64 | >128 |
| 10. | 1D-6 | $R_1 = R_2 = F$; 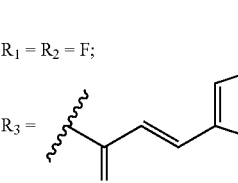 | 0.5 | 0.5 | >8 | 2 | 1 | >8 | >8 | >8 |
| 11. | 1A-4 | $R_1 = R_2 = F$; 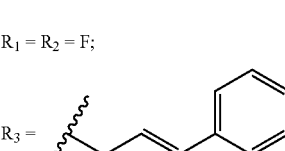 | 0.12 | 0.5 | 4 | 1 | 0.5 | >8 | >8 | >8 |
| 12. | 1A-2 | $R_1 = R_2 = F$; 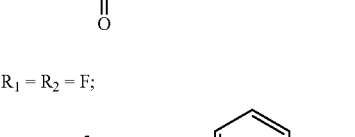 | 0.25 | 1 | 8 | 2 | 1 | >4 | >4 | >4 |
| 13. | 1A-1 | $R_1 = R_2 = F$; 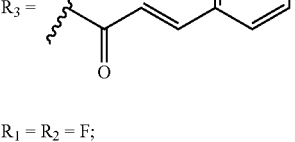 | 0.12 | 0.12 | 4 | 1 | 0.5 | >8 | >8 | >8 |
| 14. | 1A-3 | $R_1 = R_2 = F$; 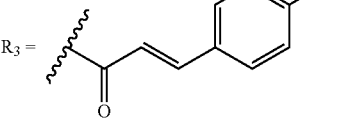 | 0.25 | 0.25 | 4 | 2 | 0.5 | >4 | >4 | >4 |
| 15. | 1B-1 | $R_1 = R_2 = F$; 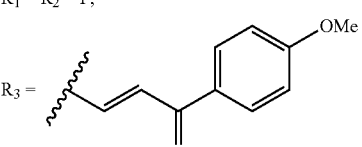 | 0.12 | 0.5 | 4 | 1 | 1 | >4 | >4 | >4 |
| 16. | 1B-4 | $R_1 = R_2 = F$; 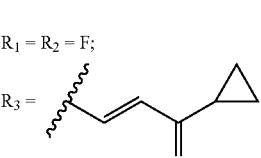 | 0.12 | 0.5 | >32 | 2 | 1 | >32 | >32 | >32 |

TABLE 4-continued
| Sr. no | Compd. no | Structure | | Ca01 | Cg01 | Ck01 | Ct01 | Cn01 | An01 | Afm01 | Fp01 |
|---|---|---|---|---|---|---|---|---|---|---|---|
| 17. | 1B-3 | $R_1 = R_2 = F$; $R_3 =$ | 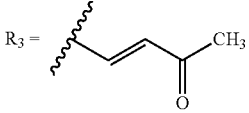 | 0.12 | 0.5 | 16 | 1 | 2 | >64 | >64 | >64 |
| 18. | 1B-2 | $R_1 = R_2 = F$; $R_3 =$ | 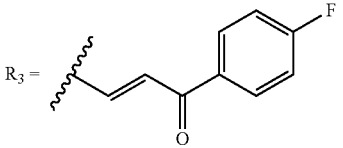 | 0.06 | 0.5 | 4 | 2 | 0.25 | >4 | >4 | >4 |
| 19. | 1B-5 | $R_1 = R_2 = F$; $R_3 =$ | 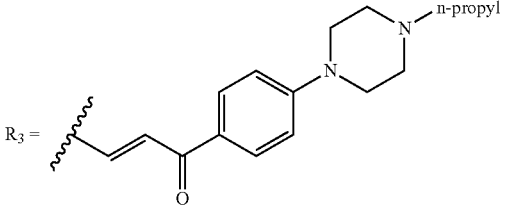 | 0.06 | 0.5 | >4 | 0.5 | 1 | >4 | >4 | >4 |
| 20. | 1B-6 | $R_1 = R_2 = F$; $R_3 =$ | 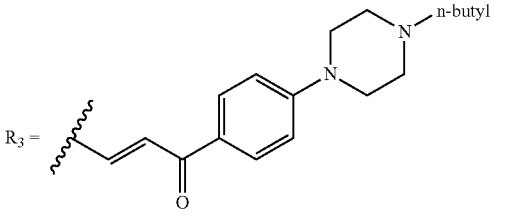 | 0.12 | 0.5 | >4 | 0.5 | 1 | >4 | >4 | >4 |
| 21. | 1B-7 | $R_1 = R_2 = F$; $R_3 =$ | 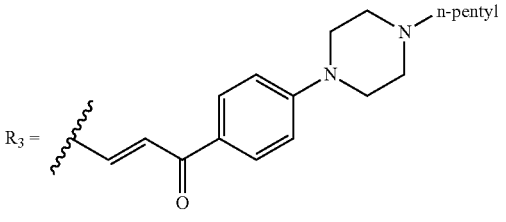 | 0.5 | 0.5 | 8 | 2 | 2 | >2 | >2 | >2 |
| 22. | 1B-9 | $R_1 = R_2 = F$; $R_3 =$ | 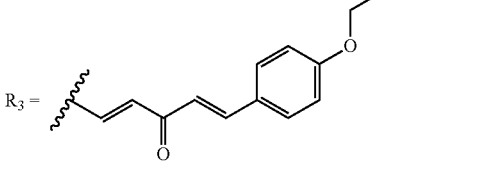 | 0.25 | 0.5 | 2 | 1 | 0.25 | >2 | >2 | >2 |
| 23. | 1B-8 | $R_1 = R_2 = F$; $R_3 =$ | 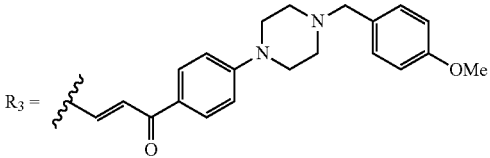 | 0.12 | 0.12 | 2 | 0.5 | 0.5 | >8 | >8 | >8 |

TABLE 4-continued

| Sr. no | Compd. no | Structure | Activity against organisms (MIC$_{50}$ in μg/ml) | | | | | | | |
|---|---|---|---|---|---|---|---|---|---|---|
| | | | Ca01 | Cg01 | Ck01 | Ct01 | Cn01 | An01 | Afm01 | Fp01 |
| 24. | 1B-10 | R$_1$ = R$_2$ = F; R$_3$ = (structure) | 0.25 | 0.5 | 2 | 1 | 1 | >2 | >2 | >2 | wherein Ca01: *C. albicans* ATCC 24433;
Cg01: *C. glabrata* ATCC 90030;
Ck01: *C. krusei* ATCC 6258;
Ct01: *C. tropicalis* ATCC 750;
Cn01: *C. neoformans* ATCC 34664;
Afm01: *A. fumigatus* ATCC 46645;
An01: *A. niger* ATCC 16404;
Fp01: *F. proliferatum* ATCC 10052.

In similar manner, individual structure moieties that form the antifungal compounds of Formula 1 of present invention, were tested for their antifungal activity against *Candida albicans, C. glabrata, C. krusei, C. tropicalis, Cryptococcus neoformans, Aspergillus fumigatus, A. niger* and *Fusarium proliferation* and the activity parameters are enumerated in Table 5.

TABLE 5

| Sr no | Compd. no | Structure | Activity against organisms (MIC$_{50}$ in μg/ml) | | | | | | | |
|---|---|---|---|---|---|---|---|---|---|---|
| | | | Ca01 | Cg01 | Ck01 | Ct01 | Cn01 | An01 | Afm01 | Fp01 |
| 1. | 8A-1 | (structure) | 32 | 2 | >128 | >128 | >128 | >128 | >128 | >128 |
| 2. | 6A-1 | (structure, n-Pr) | >4 | >4 | >4 | >4 | >4 | >4 | >4 | >4 |
| 3. | 6A-2 | (structure, n-Bu) | >4 | >4 | >4 | >4 | >4 | >4 | >4 | >4 |

TABLE 5-continued
| Sr no | Compd. no. | Structure | Activity against organisms (MIC$_{50}$ in µg/ml) | | | | | | | |
|---|---|---|---|---|---|---|---|---|---|---|
| | | | Ca01 | Cg01 | Ck01 | Ct01 | Cn01 | An01 | Afm01 | Fp01 |
| 4. | 6A-3 | 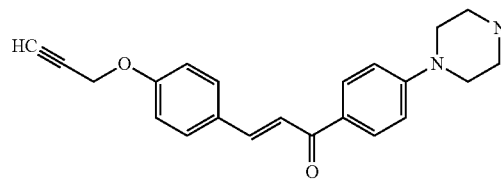 | >4 | >4 | >4 | >4 | >4 | >4 | >4 | >4 |
| 5. | 6A-4 | 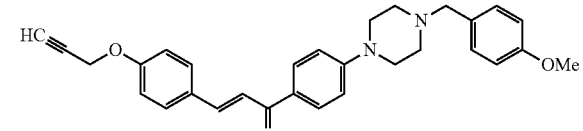 | >8 | >8 | >8 | >8 | >8 | >8 | >8 | >8 |
| 6. | 7A-1 | 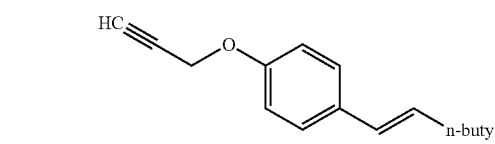 | >4 | >4 | >4 | >4 | >4 | >4 | >4 | >4 |
| 7. | 7A-2 | 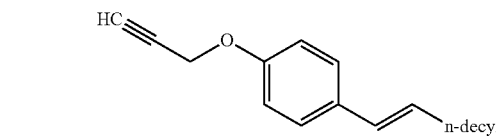 | >8 | >8 | >8 | >8 | >8 | >8 | >8 | >8 |
| 8. | 9A-1 | 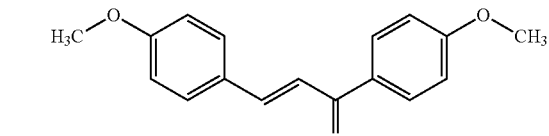 | >4 | >4 | >4 | >4 | >4 | >4 | >4 | >4 |
| 9. | 9A-2 | 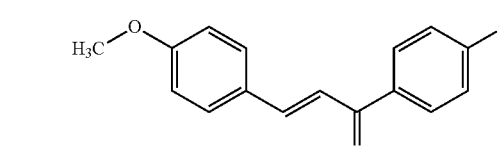 | >32 | >32 | >32 | >32 | >32 | >32 | >32 | >32 |
| 10. | 9A-3 | 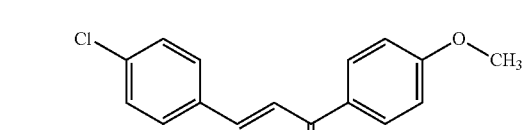 | >4 | >4 | >4 | >4 | >4 | >4 | >4 | >4 |
| 11. | 9A-4 | 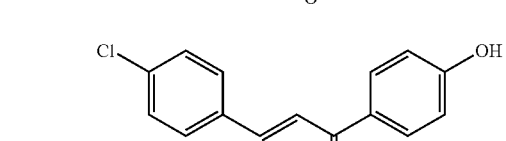 | >8 | 32 | >8 | >8 | >8 | >8 | >8 | >8 |
| 12. | 9A-5 | 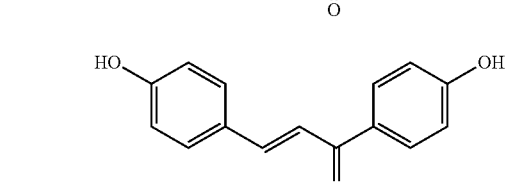 | 32 | 16 | >32 | >32 | 32 | 8 | 16 | >32 |

TABLE 5-continued

| Sr no | Compd. no | Structure | Activity against organisms (MIC$_{50}$ in μg/ml) | | | | | | | |
|---|---|---|---|---|---|---|---|---|---|---|
| | | | Ca01 | Cg01 | Ck01 | Ct01 | Cn01 | An01 | Afm01 | Fp01 |
| 13. | 10A-1 | (thiophene-CH=CH-C(=O)-C6H4-OH) | >32 | >32 | >32 | >32 | >32 | >32 | >32 | >32 |
| 14. | 10A-2 | (thiophene-CH=CH-C(=O)-C6H4-OCH3) | >8 | >8 | >8 | >8 | >8 | >8 | >8 | >8 |
| 15. | 11A-1 | (H3C-C(=O)-C6H4-N(piperazine)N-Pr) | >128 | >128 | >128 | >128 | >128 | >128 | >128 | >128 |
| 16. | 11A-2 | (H3C-C(=O)-C6H4-N(piperazine)N-n-Bu) | >64 | >64 | >64 | >64 | >64 | >64 | >64 | >64 | wherein Ca01: *C. albicans* ATCC 24433;
Cg01: *C. glabrata* ATCC 90030;
Ck01: *C. krusei* ATCC 6258;
Ct01: *C. tropicalis* ATCC 750;
Cn01: *C. neoformans* ATCC 34664;
Afm01: *A. fumigatus* ATCC 46645;
An01: *A. niger* ATCC 16404;
Fp01: *F. proliferatum* ATCC 10052.

The results enumerated in Table 5 indicate that individual structure moieties that form the antifungal compounds of Formula 1 of present invention do not possess antifungal activities. From the results of antifungal activity testing indicated in Tables 4 and 5, it is clearly understood that even though individual structure moieties that form the antifungal compounds of Formula 1 of present invention, do not possess antifungal activity, the resulting compounds of Formula 1 do possess antifungal activity wherein some of the compounds of Formula 1 exhibit antifungal activity superior to fluconazole, and hence coupling of these structure moieties to form compounds of Formula 1 of the present invention shows better synergy in terms of antifungal activity and hence, is not obvious for a person skilled in art. It is noted that compounds of present invention exhibit very good antifungal activity against *Candida albicans* and *Candida glabrata*. It is also noted that fluconazole exhibits weaker antifungal activity against *Candida tropicalis* and *Cryptococcus neoformans* while some of the compounds of present invention exhibit significant antifungal activity against these fungi.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An antifungal compound of Formula 1, or a pharmaceutically acceptable salt thereof, Formula 1

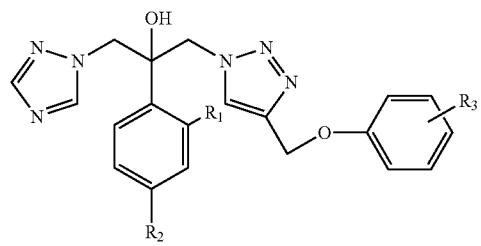

wherein $R_1$ and $R_2$ are independently selected from the group consisting or hydrogen and a halogen;

$R_3$ is selected from the group consisting of hydrogen, a halogen, a substituted or unsubstituted alkyl having a linear or branched chain of 1 to 20 carbon atoms, a substituted or unsubstituted aryl, nitro, a substituted or unsubstituted alkylamino, a substituted or unsubstituted arylamino, a substituted or unsubstituted heteroarylamino, $C(O)R_4$, —COCH═CHR$_5$, —CH═CH—COR$_6$, or a substituted or unsubstituted alkenyl;

$R_4$ is selected from the group consisting of hydrogen, a substituted or unsubstituted alkyl having a linear or branched chain of 1 to 20 carbon atoms, and a substituted or unsubstituted alkenyl having a linear or branched chain of 1 to 20 carbon, atoms; and $R_5$ selected from the group consisting of a substituted or unsubstituted alkyl, a substituted or unsubstituted aryl, and a substituted or unsubstituted heteroaryl.

2. The antifungal compound as claimed in claim 1, wherein at least one or $R_1$ and $R_2$ is a halogen, said halogen being selected from the group consisting of fluorine, chlorine, and bromine.

3. The antifungal compound as claimed in claim 1, wherein $R^1$ and $R^2$ each represent fluorine.

4. The antifungal compound as claimed in claim 1, wherein $R_3$ is a substituted alkenyl.

5. The antifungal compound as claimed in claim 1, wherein $R_3$ is a substituted alkenyl of formula —CH═CH—$R_6$ wherein $R_6$ is selected from the group consisting of a substituted or unsubstituted alkyl, a substituted or unsubstituted aryl, and a substituted or unsubstituted heteroaryl.

6. An antifungal compound selected from the group consisting of:
- (E)-1-(4-((1-(2-(2,4-Diflourophenyl)-2-hydroxy-3-(1H-1,2,4-triazol-1-yl)propyl)-1H-1,2,3-triazol-4-yl)methoxy)phenyl)-3-phenylprop-2-en-1-one;
- (E)-1-(4-((1-(2-(2,4-diflourophenyl)-2-hydroxy-3-(1H-1,2,4-triazol-1-yl)propyl)-1H-1,2,3-triazol-4-yl)methoxy)phenyl)-3-(4-methoxyphenyl)prop-2-en-1-one;
- (E)-1-(4-((1-(2-(2,4-Diflourophenyl)-2-hydroxy-3-(1H-1,2,4-triazol-1-yl)propyl)-1H-1,2,3-triazol-4-yl)methoxy)phenyl)-3-(4-methylphenyl)prop-2-en-1-one;
- (E)-1-(4-((1-(2-(2,4-Diflourophenyl)-2-hydroxy-3-(1H-1,2,4-triazol-1-yl)propyl)-1H-1,2,3-triazol-4-yl)methoxy)phenyl)-3-(2-thienyl)prop-2-en-1-one;
- (E)-1-(4-((1-(2-(2,4-Diflourophenyl)-2-hydroxy-3-(1H-1,2,4-triazol-1-yl)propyl)-1H-1,2,3-triazol-4-yl)methoxy)phenyl)-1-(4-methoxyphenyl)prop-2-en-1-one;
- (E)-3-(4-((1-(2-(2,4-Diflourophenyl)-2-hydroxy-3-(1H-1,2,4-triazol-1-yl)propyl)-1H-1,2,3-triazol-4-yl)methoxy)phenyl)-1-(4-fluorophenyl)prop-2-en-1-one;
- (E)-4-(4-((1-(2-(2,4-Diflourophenyl)-2-hydroxy-3-(1H-1,2,4-triazol-1-yl)propyl)-1H-1,2,3-triazol-4-yl)methoxy)phenyl)but-3-en-2-one;
- (E)-1-(Cyclopropyl)-3-(4-((1-(2-(2,4-diflourophenyl)-2-hydroxy-3-(1H-1,2,4-triazol-1-yl)propyl)-1H-1,2,3-triazol-4-yl)methoxy)phenyl)prop-2-en-1-one;
- (E)-3-(4-((1-(2-(2,4-Diflourophenyl)-2-hydroxy-3-(1H-1,2,4-triazol-1-yl)propyl)-1H-1,2,3-triazol-4-yl)methoxy)phenyl)-1-(4-(4-propylpiperazin-1-yl)phenyl)prop-2-en-1-one;
- (E)-1-(4-(4-n-Butylpiperazin-1-yl)phenyl)-3-(4-((1-(2-(2,4-Diflourophenyl)-2-hydroxy-3-(1H-1,2,4-triazol-1-yl)propyl)-1H-1,2,3-triazol-4-yl)methoxy)phenyl)prop-2-en-1-one;
- (E)-3-(4-((1-(2-(2,4-Diflourophenyl)-2-hydroxy-3-(1H-1,2,4-triazol-1-yl)propyl)-1H-1,2,3-triazol-4-yl)methoxy)phenyl)-1-(4-(4-n-pentylpiperazin-1-yl)phenyl)prop-2-en-1-one;
- (E)-3-(4-((1-(2-(2,4-Diflourophenyl)-2-hydroxy-3-(1H-1,2,4-triazol-1-yl)propyl)-1H-1,2,3-triazol-4-yl)methoxy)phenyl)-1-(4-(4-(4-methoxybenzyl)piperazin-1-yl)phenyl)prop-2-en-1-one;
- (1E,4E)-1-(4-(Buta-2,3-dienyloxy)phenyl)-5-(4-((1-(2-(2,4-difluorophenyl)-2-hydroxy-3-(1H-1,2,4-triazol-1-yl)propyl)-1H-1,2,3-triazol-4-yl)methoxy)phenyl)penta-1,4-dien-3-one;
- (E)-1-(4-(2-(2,4-Diflourophenyl)-2-hydroxy-3-(1H-1,2,4-triazol-1-yl)propoxy)phenyl)-3-(4-((1-(2-(2,4-difluorophenyl)-2-hydroxy-3-(1H-1,2,4-triazol-1-yl)propyl)-1H-1,2,3-triazol-4-yl)methoxy)phenyl)prop-2-en-1-one;
- (E)-1-(4-((4-(But-1-en-1-yl)phenoxy)methyl)-1H-1,2,3-triazol-1-yl)-2-(2,4-difluorophenyl)-3-(1H-1,2,4-triazol-1-yl)propan-2-ol;
- (E)-2-(2,4-Diflourophenyl)-1-(4-((4-(n-hex-1-en-1-yl)phenoxy)methyl)-1H-1,2,3-triazol-1-yl)-3-(1H-1,2,4-triazol-1-yl)propan-2-ol;
- (E)-2-(2,4-Diflourophenyl)-1-(4-((4-(n-dodec-1-en-1-yl)phenoxy)methyl)-1H-1,2,3-triazol-1-yl)-3-(1H-1,2,4-triazol-1-yl)propan-2-ol;
- (E)-2-(2,4-Diflourophenyl)-1-(4-((4-(prop-1-en-1-yl)phenoxy)methyl)-1H-1,2,3-triazol-1-yl)-3-(1H-1,2,4-triazol-1-yl)propan-2-ol;
- 2-(2,4-Diflourophenyl)-1-(4-phenyloxymethyl-1H-1,2,3-triazol-1-yl)-3-1,2,4-triazol-1-yl)propan-2-ol;
- 4-((1-(2-(2,4-diflourophenyl)-2-hydroxy-3-(1H-1,2,4-triazol-1-yl)propyl-1H-1,2,3-triazol-4-yl)methoxy)benzaldehyde;
- 2-(2,4-Difluorophenyl)-1-(4-(4-acetylphenyloxy)methyl-1H-1,2,3-triazol-1-yl)-3-(1H-1,2,4-triazol-1-yl)propan-2-ol;
- 1-(4-(4-Acetylaminophenyloxy)methyl-1H-1,2,3-triazol-1-yl)-2-2,4-difluorophenyl)-3-(1H-1,2,4-triazol-1-yl)propan-2-ol;
- 2-(2,4-Difluorophenyl)-1-(4-(4-methylphenyloxy)methyl-1H-1,2,3-triazol-1-yl)-3-(1H-1,2,4-triazol-1-yl)propan-2-ol; and
- 3-Amino-4'-((1-(2-(2,4-difluorophenyl)-2-hydroxy-3-(1H-1,2,4-triazol-1-yl)propyl)-1H-1,2,3-triazol-4-yl)methoxy)-6-methylbiphenyl-2,4-dicarbonitrile.

7. A process for preparation of the antifungal compound as claimed in claim 1, composing:

reacting a mixture of an azide of Formula 2 with a compound of Formula 3 in a solvent, said reacting being carried out (a) in the presence of copper sulphate and sodium ascorbate, (b) with exposure to microwave radiation, or by heating the mixture with stirring,

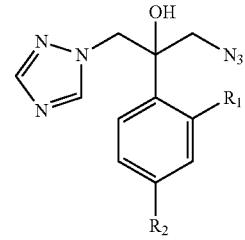

Formula 2

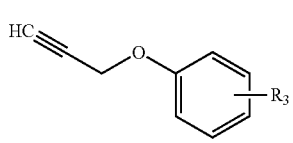

Formula 3 wherein, $R_1$, $R_2$, $R_3$, $R_4$ and $R_5$ are as defined in claim 1.

8. The process as claimed in claim 7, wherein the solvent is selected from the group consisting of dimethyl formamide, dioxane, ethanol, methanol, water, acetonitrile, and mixtures thereof.

9. A process for preparation of the antifungal compound as claimed in claim 1, comprising:

reacting a mixture of an azide of Formula 2, wherein $R_3$ is —C(O)$R_4$, with a compound of Formula 3 in a solvent, said reacting being carried out (a) in the presence of copper sulphate and sodium ascorbate, (b) with exposure to microwave radiation, or by heating the mixture with stirring;

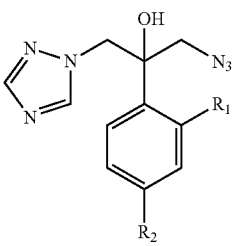

Formula 2

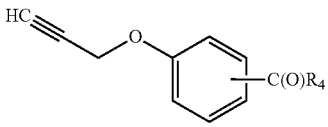

Formula 3 wherein $R_4$ is hydrogen or methyl, to obtain a compound of formula 4; and

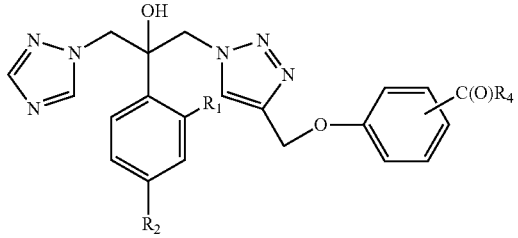

Formula 4 reacting the compound of formula 4 with an aldehyde or a ketone in the presence of a base, an acid, or an amino acid to form the compound of Formula 1.

10. The process as claimed in claim 9, wherein the solvent is selected from the group consisting of dimethyl formamide, dioxane, ethanol, methanol, water, acetonitrile, and mixtures thereof.

11. The process as claimed in claim 9, wherein the base is selected from the group consisting of sodium hydroxide, potassium hydroxide, ammonium acetate, ammonium formate, morpholine, and mixtures thereof.

12. The process as claimed in claim 9, wherein the acid is acetic acid or propanoic acid.

13. The process as claimed in claim 9, wherein the amino acid is proline or alanine.

14. A pharmaceutical composition for treating or preventing a fungal infection in a subject, comprising the antifungal compound of claim 1 and at least one pharmaceutically acceptable excipient.

15. A method of treating or preventing a fungal infection in a subject, comprising administering the antifungal compound of claim 1 to said subject.

16. A method of treating or preventing a fungal infection in a subject, comprising administering the pharmaceutical composition of claim 14 to said subject.

\* \* \* \* \*

UNITED STATES PATENT AND TRADEMARK OFFICE
CERTIFICATE OF CORRECTION

Page 1 of 1

PATENT NO. : 9,540,350 B2
APPLICATION NO. : 14/771991
DATED : January 10, 2017
INVENTOR(S) : Hanumant Barpurao Borate et al.

It is certified that error appears in the above-identified patent and that said Letters Patent is hereby corrected as shown below:

In the Claims

In Column 47, Line 10, please delete: "-C(O)R$_4$, -COCH=CHR$_5$, -CH=CH-COR$_6$"
and substitute therefor the following: -C(O)R$_4$, -COCH=CHR$_5$, -CH=CH-COR$_5$ Signed and Sealed this
Twenty-fifth Day of April, 2017

Michelle K. Lee
*Director of the United States Patent and Trademark Office*